(12) United States Patent
Tagami et al.

(10) Patent No.: US 6,818,327 B2
(45) Date of Patent: Nov. 16, 2004

(54) ORGANIC ELECTROLUMINESCENCE DEVICE

(75) Inventors: Sanae Tagami, Sodegaura (JP); Hidetsugu Ikeda, Sodegaura (JP); Chishio Hosokawa, Sodegaura (JP); Takashi Arakane, Sodegaura (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 0 days.

(21) Appl. No.: 10/244,164

(22) Filed: Sep. 16, 2002

(65) Prior Publication Data

US 2003/0054200 A1 Mar. 20, 2003

Related U.S. Application Data

(62) Division of application No. 09/675,201, filed on Sep. 29, 2000.

(30) Foreign Application Priority Data

Sep. 30, 1999 (JP) .......................................... 11-279462

(51) Int. Cl.[7] .......................... H05B 33/12; C09K 11/06
(52) U.S. Cl. ....................... 428/690; 428/917; 313/504; 313/506; 252/301.16
(58) Field of Search ................................ 428/690, 917; 313/504, 506; 252/301.16

(56) References Cited

U.S. PATENT DOCUMENTS 6,127,516 A  10/2000  Bard et al. .................. 528/396

FOREIGN PATENT DOCUMENTS

| JP | 10-125467 | 5/1998 |
| JP | 10-168445 | 6/1998 |
| JP | 10189248 | 7/1998 |
| JP | 10-294177 | 11/1998 |
| JP | 10-340782 | 12/1998 |
| JP | 10-340783 | 12/1998 |
| JP | 11-040360 | 2/1999 |
| JP | 11-168445 | 6/1999 |
| JP | 11-176575 | * 7/1999 |
| JP | 2000-026324 | 1/2000 |

OTHER PUBLICATIONS

Matsuda, Masanori et al., Chemistry Letters (2), pp. 157–158, (1996).*

"Properties and Infrared Spectra in the Potassium Bromide Region of 8–quinolinol and Its Metal Chelates", Tackett et al., Inorganic Chemistry, May 1964, vol. 3, No. 5, pp. 692–696.*

* cited by examiner

*Primary Examiner*—Dawn Garrett
(74) *Attorney, Agent, or Firm*—Oblon, Spivak, McClelland, Maier & Neustadt, P.C.

(57) ABSTRACT

An organic electroluminescence device which exhibits an excellent purity of color and a high efficiency of light emission, has a long life and emits reddish light and a novel compound having these characteristics are provided. The organic electroluminescence device comprises an organic layer disposed between at least one pair of electrodes, wherein the organic layer comprises a compound having a fluoranthene skeleton structure substituted at least with an amine group or an alkenyl group.

8 Claims, 3 Drawing Sheets

ORGANIC ELECTROLUMINESCENCE DEVICE

TECHNICAL FIELD

The present invention relates to an organic electroluminescence device which is used as a light source such as a planar light emitting member of televisions and a back light of displays, exhibits an excellent purity of color and a high efficiency of light emission, has a long life and emits reddish light and to a novel compound having these characteristics.

BACKGROUND ART

Electroluminescence (referred to as EL, hereinafter) devices using organic compounds are expected to be used for inexpensive full color display devices of the solid light emission type which can display a large area and development thereof has been actively conducted. In general, an EL device is constituted with a light emitting layer and a pair of electrodes faced to each other at both sides of the light emitting layer. When a voltage is applied between the electrodes, electrons are injected at the side of the cathode and holes are injected at the side of the anode. The electrons are combined with the holes in the light emitting layer and an excited state is formed. When the excited state returns to the normal state, the energy is emitted as light.

Although the practical application of organic EL devices has started recently, devices for full color displays are still under development. In particular, a material for organic EL devices which exhibits an excellent purity of color and a high efficiency of light emission, has a long life and emits reddish light has been desired.

In an attempt to satisfy the above desire, a device emitting red light in which a derivative of naphthacene or pentacene is added to a light emitting layer is disclosed in Japanese Patent Application Laid-Open No. Heisei 8(1996)-311442. Although this device exhibits an excellent purity of red light, the device exhibits an efficiency of light emission as low as 0.7 lm/W and has an insufficient average life which is shorter than 150 hours. An average life of at least several thousand hours is necessary for practical applications. A device in which a compound derived from dicyanomethylene (DCM) is added to a light emitting layer is disclosed in Japanese Patent Application Laid-Open No. Heisei 3(1991)-162481. However, this device exhibits an insufficient purity of red light. In Japanese Patent Application Laid-Open Nos. Heisei 10(1998)-340782 and Heisei 11(1999)-40360, organic EL devices using fluoranthene compounds are disclosed. However, the devices using the compounds disclosed in the above patent applications do not emit yellow to red light. The efficiency of light emission is as small as 4 cd/A or smaller and insufficient.

DISCLOSURE OF THE INVENTION

The present invention has been made to overcome the above problems and has an object of providing an organic EL device which exhibits an excellent purity of color and a high efficiency of light emission, has a long life and emits reddish light and a novel compound having these characteristics.

As the result of extensive studies by the present inventors to develop an organic electroluminescence device (referred to as an organic EL device, hereinafter) having the above advantageous properties, it was found that the object can be achieved by using a compound having a fluoranthene skeleton structure substituted at least with an amine group or an alkenyl group as the light emitting material.

The organic electroluminescence device of the present invention comprises an organic layer disposed between at least one pair of electrodes, wherein the organic layer comprises a compound having a fluoranthene skeleton structure substituted at least with an amine group or an alkenyl group.

It is preferable that the above compound is a compound selected from compounds represented by the following general formulae [1] to [18]:

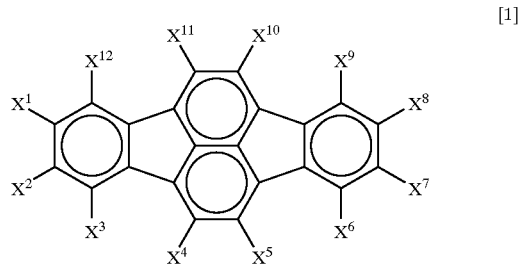

[1]

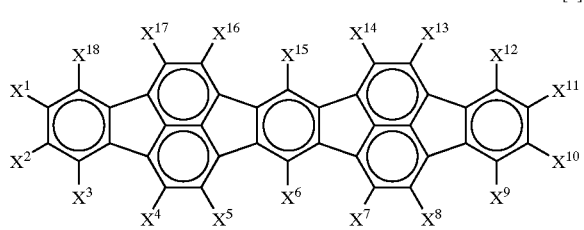

[2]

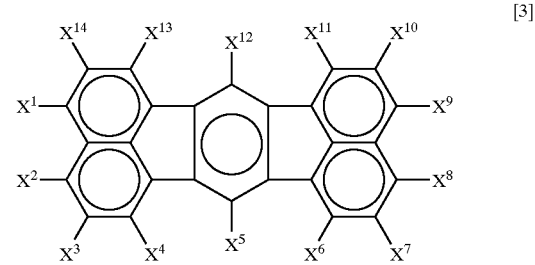

[3]

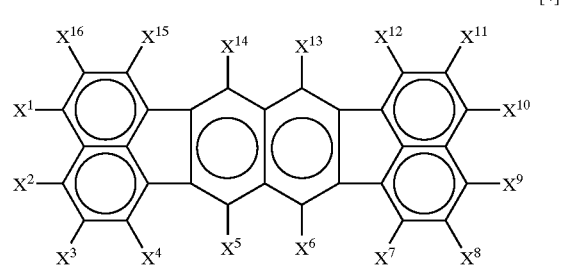

[4]

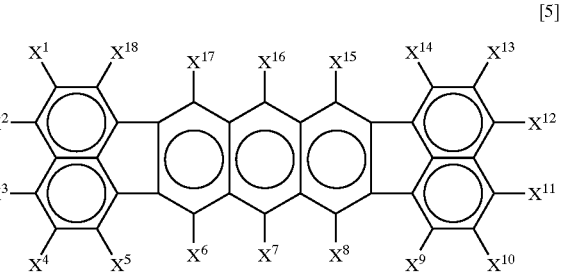

[5]

-continued
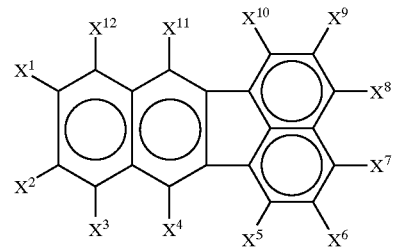
[6]
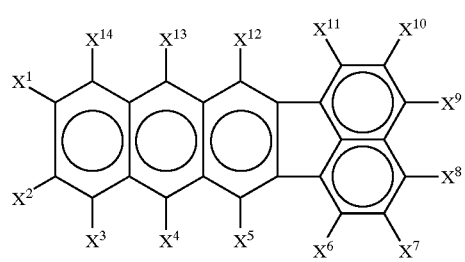
[7]
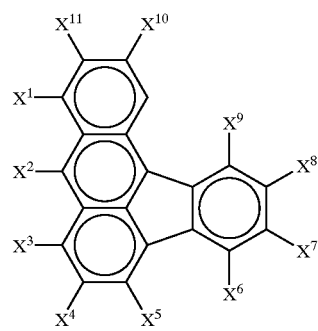
[8]
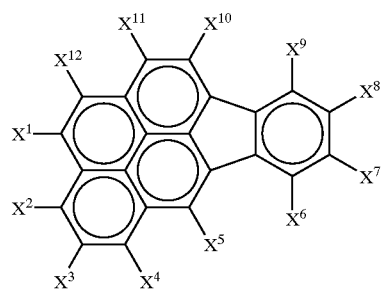
[9]
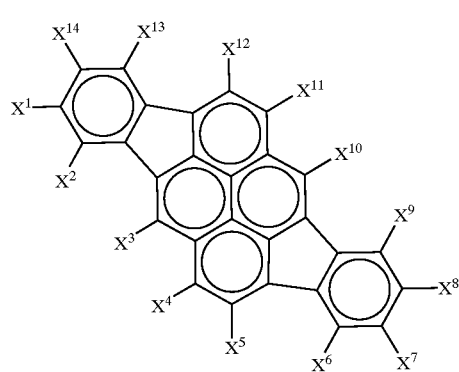
[10]
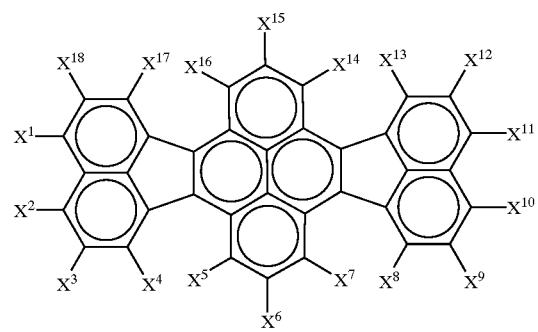
[11]
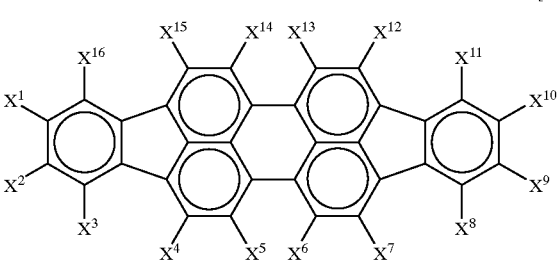
[12]
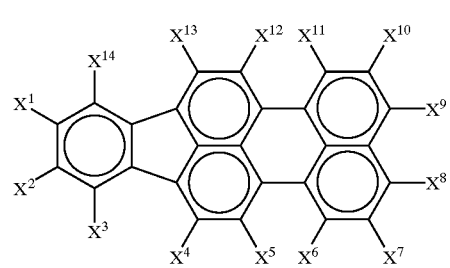
[13]
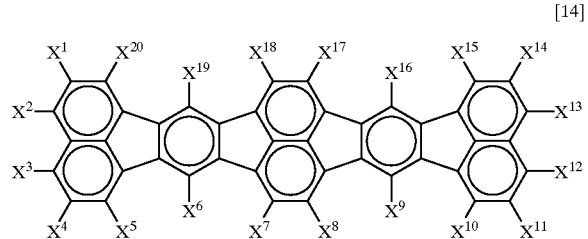
[14]
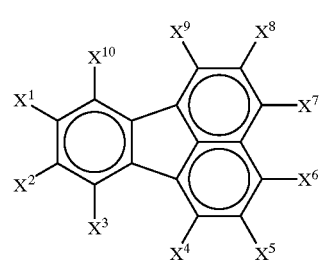
[15]

-continued

[16]

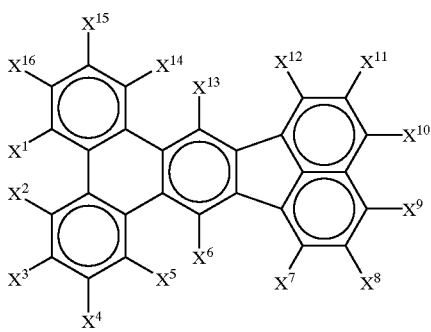

wherein $X^1$ to $X^{20}$ each independently represents hydrogen atom, a linear, branched or cyclic alkyl group having 1 to 20 carbon atoms, a linear, branched or cyclic alkoxy group having 1 to 20 carbon atoms, a substituted or unsubstituted aryl group having 6 to 30 carbon atoms, a substituted or unsubstituted aryloxy group having 6 to 30 carbon groups, a substituted or unsubstituted arylamino group having 6 to 30 carbon atoms, a substituted or unsubstituted alkylamino group having 1 to 30 carbon atoms, a substituted or unsubstituted arylalkylamino group having 7 to 30 carbon atoms or a substituted or unsubstituted alkenyl groups having 8 to 30 carbon atoms; a pair of adjacent groups represented by $X^1$ to $X^{20}$ and a pair of adjacent substituents to groups represented by $X^1$ to $X^{20}$ may form a cyclic structure in combination; when a pair of adjacent substituents are aryl groups, the pair of substituents may be a single group; and at least one of substituents represented by $X^1$ to $X^i$, i representing a number of 12 to 20, comprises an amine group or an alkenyl group;

[17]

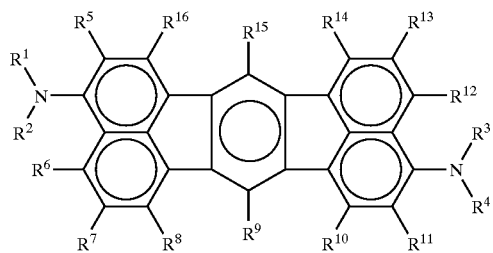

[18]

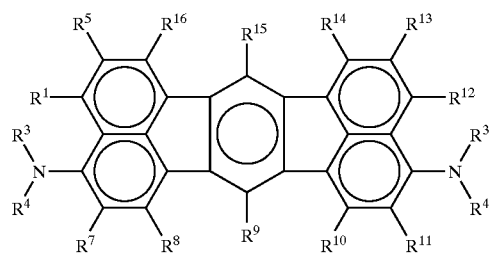

wherein $R^1$ to $R^4$ each independently represent an alkyl group having 1 to 20 carbon atoms or a substituted or unsubstituted aryl group having 6 to 30 carbon atoms; in one or both of a pair of groups represented by $R^1$ and $R^2$ and a pair of groups represented by $R^3$ and $R^4$, the groups forming the pair may be bonded through —O— or —S—; $R^5$ to $R^{16}$ represents hydrogen atom, a linear, branched or cyclic alkyl group having 1 to 20 carbon atoms, a linear, branched or cyclic alkoxy group having 1 to 20 carbon atoms, a substi- tuted or unsubstituted aryl group having 6 to 30 carbon atoms, a substituted or unsubstituted aryloxy group having 6 to 30 carbon groups, a substituted or unsubstituted arylamino group having 6 to 30 carbon atoms, a substituted or unsubstituted alkylamino group having 1 to 30 carbon atoms, a substituted or unsubstituted arylalkylamino group having 7 to 30 carbon atoms or a substituted or unsubstituted alkenyl groups having 8 to 30 carbon atoms; a pair of adjacent groups represented by $R^5$ to $R^{16}$ and a pair of adjacent substituents to groups represented by $R^5$ to $R^{16}$ may form a cyclic structure in combination; and at least one of substituents represented by $R^5$ to $R^{16}$ comprises an amine group or an alkenyl group.

The novel compound of the present invention is a compound represented by any of the above general formulae [1] to [18].

THE MOST PREFERRED EMBODIMENT TO CARRY OUT THE INVENTION

Figure 1:
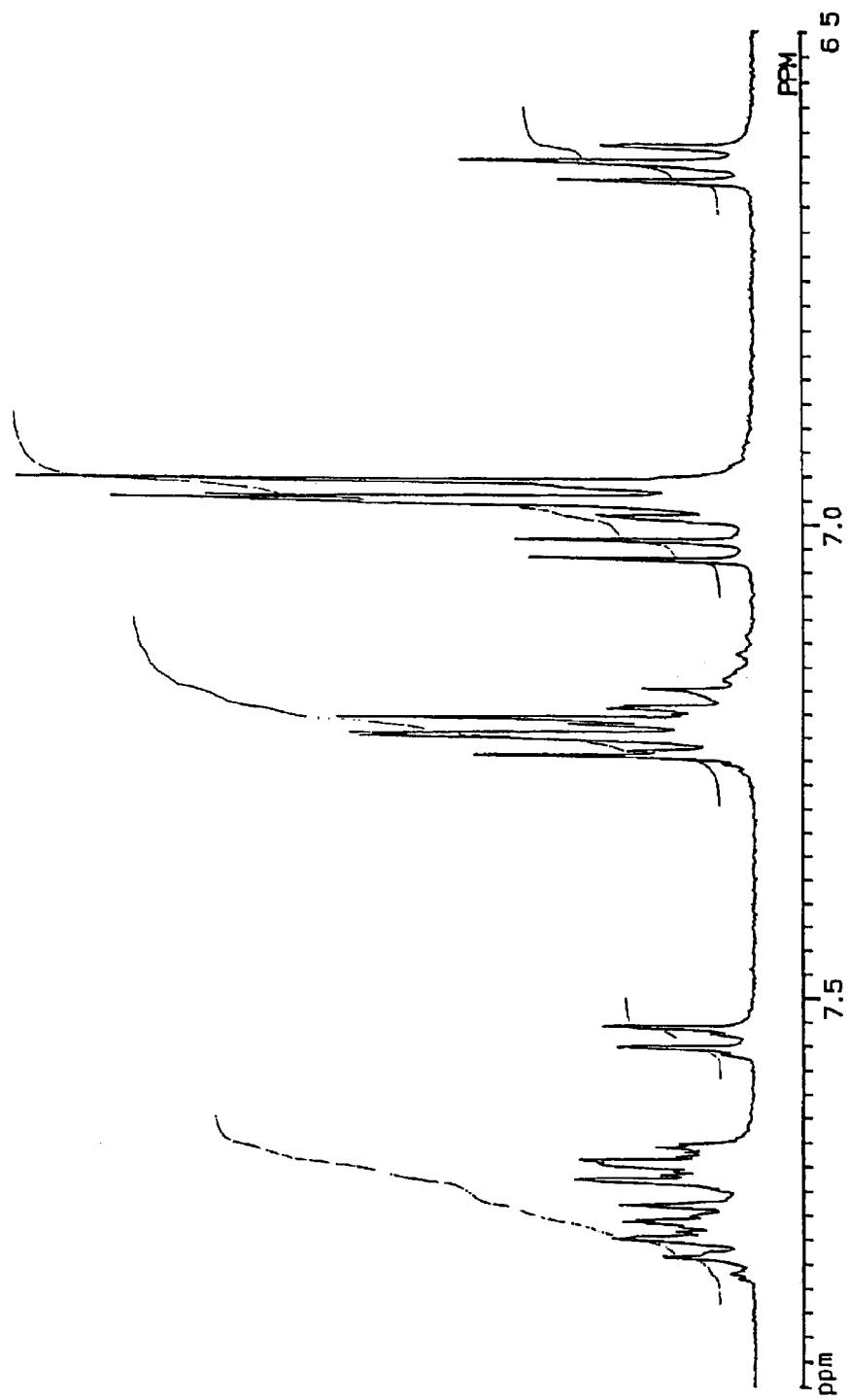
FIG. 1 shows the $^1$H-NMR spectrum of an example of the novel compound of the present invention.

The organic electroluminescence device of the present invention comprises an organic layer disposed between at least one pair of electrodes, wherein the organic layer comprises compounds having a fluoranthene skeleton structure substituted at least with an amine group or an alkenyl group.

This compound is a novel compound and is represented by any of the above general formulae [1] to [18].

In general formulae [1] to [16], $X^1$ to $X^{20}$ each independently represents hydrogen atom, a linear, branched or cyclic alkyl group having 1 to 20 carbon atoms, a linear, branched or cyclic alkoxy group having 1 to 20 carbon atoms, a substituted or unsubstituted aryl group having 6 to 30 carbon atoms, a substituted or unsubstituted aryloxy group having 6 to 30 carbon groups, a substituted or unsubstituted arylamino group having 6 to 30 carbon atoms, a substituted or unsubstituted alkylamino group having 1 to 30 carbon atoms, a substituted or unsubstituted arylalkylamino group having 7 to 30 carbon atoms or a substituted or unsubstituted alkenyl groups having 8 to 30 carbon atoms; a pair of adjacent groups represented by $X^1$ to $X^{20}$ and a pair of adjacent substituents to groups represented by $X^1$ to $X^{20}$ may form a cyclic structure in combination; when a pair of adjacent substituents are aryl groups, the pair of substituents may be a single group; and at least one of substituents represented by $X^1$ to $X^i$, i representing a number of 12 to 20, comprises an amine group or an alkenyl group. That a pair of adjacent substituents may be a single group when the pair of adjacent substituents are aryl groups means that the adjacent bonds for the pair of substituents are bonded to the same single divalent aromatic ring group.

In general formulae [17] and [18], $R^1$ to $R^4$ each independently represent an alkyl group having 1 to 20 carbon atoms or a substituted or unsubstituted aryl group having 6 to 30 carbon atoms; in one or both of a pair of groups represented by $R^1$ and $R^2$ and a pair of groups represented by $R^3$ and $R^4$, the groups forming the pair may be bonded through —O— or —S—; $R^5$ to $R^{16}$ represents hydrogen atom, a linear, branched or cyclic alkyl group having 1 to 20 carbon atoms, a linear, branched or cyclic alkoxy group having 1 to 20 carbon atoms, a substituted or unsubstituted aryl group having 6 to 30 carbon atoms, a substituted or unsubstituted aryloxy group having 6 to 30 carbon groups, a substituted or unsubstituted arylamino group having 6 to 30 carbon atoms, a substituted or unsubstituted alkylamino group having 1 to 30 carbon atoms, a substituted or unsubstituted arylalkylamino group having 7 to 30 carbon atoms or a substituted or unsubstituted alkenyl groups having 8 to 30 carbon atoms; a pair of adjacent groups represented by $R^5$ to $R^{16}$ and a pair of adjacent substituents to groups represented by $R^5$ to $R^{16}$ may form a cyclic structure in combination; and at least one of substituents represented by $R^5$ to $R^{16}$ comprises an amine group or an alkenyl group.

Preferable compounds among the compounds represented by general formulae [1] to [18] are shown in the following.

It is preferable that the fluoranthene skeleton structure comprises at least 5 condensed rings and more preferably at least 6 condensed rings. By using the compounds having this structure, light having a longer wave length such as yellowish to reddish light can be emitted.

It is preferable that the fluoranthene skeleton structure is substituted with an amino group. By using the compound having this structure, a light emitting material having a longer life can be obtained.

It is preferable that the amino group is a substituted or unsubstituted arylamino group and more preferably a substituted or unsubstituted diarylamino group. By using the compound having this structure, a device showing a smaller decrease in the light emission at increased concentrations of the compound and exhibiting a high efficiency can be obtained even when the above compound is added to the light emitting layer in a concentration as high as 2% or higher.

It is preferable that the above compound has a symmetric structure having an axial symmetry or a symmetry with respect to plane. By using the compound having this structure, durability of the device is improved and the quantum efficiency of fluorescence is enhanced.

It is preferable that the above compound has at least ten six-membered rings or five-membered rings. The compound has a glass transition temperature of 100° C. or higher due to this structure and heat stability of a layer composed of or comprising this compound is improved. It is preferable that the above compound has an aryl group, a cyclic alkyl group, an aryloxy group, an arylthio group or an arylalkyl group each having 4 or more carbon atoms. Since these groups exhibit steric hindrance and the decrease in the light emission at increased concentrations of the compound can be prevented.

It is preferable that, in general formulae [17] and [18], $R^{15}$ and $R^9$ each represent a group having a substituent. When the compound represented by general formula [17] or [18] has this structure, the compound has an improved stability against oxidation and reduction and the life of the device can be extended.

When the fluoranthene skeleton structure is substituted with two amino groups, two alkenyl groups or a combination of an amino group and an alkenyl group, the compound having this fluoranthene skeleton structure has isomers.

Examples of the isomers are described in the case where the fluoranthene skeleton structure is 7,14-diphenylacenaphtho[1,2-k]-fluoranthene.

Dibromo-substituted acenaphtho[1,2-k]fluoranthene has two isomers, i.e., 3,10-dibromo-7,14-diphenylacenaphtho[1,2-k]fluoranthene (isomer A) and 3,11-dibromo-7,14-diphenylacenaphtho[1,2-k]fluoranthene (isomer B).

The final product obtained from isomer A and isomer B as the intermediates contains an amino-substituted compound derived from isomer A and an amino-substituted compound derived from isomer B. When the final product is prepared, the relative amounts of isomer A and isomer B contained in the final product is different depending on the process of the preparation. (1) The dibromo-substituted compounds may be obtained from a solution portion of a reaction mixture in which the dibromo-substituted compounds are dissolved. (2) The dibromo-substituted compounds may also be obtained from precipitates formed by recrystallization from a solution which is obtained by dissolving the product obtained above from the solution portion of the reaction mixture. (3) The dibromo-substituted compounds may also be obtained from the solution left after the above recrystallization. By suitably selecting the process and the type of the solvent used for the treatment, the object compound containing various amounts of isomer A and isomer B and, specifically, having a ratio of the amount by mole of isomer A to the amount in mole of isomer B in the range of 10:90 to 90:10, can be obtained.

It is preferable that the error in the ratio of the amounts by mole of the isomers is: (i) isomer A:isomer B=x±10:y±10 (x±y=100) and more preferably (ii) isomer A:isomer B=x±5:y±5 (x±y=100). When the relation (i) is satisfied, the ratio of the amounts of the isomers will be described as approximately constant and, when the relation (ii) is satisfied, the ratio of the amounts of the isomers will be described as constant, hereinafter.

When the above compound of the present invention has isomers, a plurality of isomers can be comprised in the organic layer. It is preferable that the device is prepared under the condition that the ratio of the amounts of the isomers is kept approximately constant or constant. By preparing the device in this manner, the spectrum of the light emitted from the device can be kept the same. In other words, the color of the emitted light can be kept the same. Moreover, the color of the emitted light can be changed by changing the ratio of the amounts of the isomers. Naturally, the organic layer may comprise a single compound with exclusion of any other isomers.

When a compound contains isomers as described above, one of the isomers can emit light having a longer wavelength than that of light emitted from other isomers. Therefore, light having a longer wavelength such red light can be emitted when the ratio of the amount by mole of the isomer which can emit light having a longer wavelength to the amount by mole of the isomer which can emit light having a shorter wavelength is preferably in the range of 90:10 to 60:40 and more preferably in the range of 99:1 to 70:30.

Taking advantage of the difference in the chemical shift in $^1$H-NMR between the isomers, the ratio of the amounts of the isomers can be calculated from the ratio of the areas of peak signals assigned to each isomer.

It is preferable that the organic layer is at least one of a hole transportation layer and a light emitting layer.

A layer of an inorganic compound may be disposed between the organic layer and the electrode.

The organic EL device of the present invention emits reddish light.

Examples of the compounds represented by general formulae [1] to [18] of the present invention include (A-1) to (A-18) and (B-1) to (B-17) which are shown in the following. However, the present invention is not limited to these compounds shown as the examples. In the formulae shown in the following, Me means methyl group and Et means ethyl group.

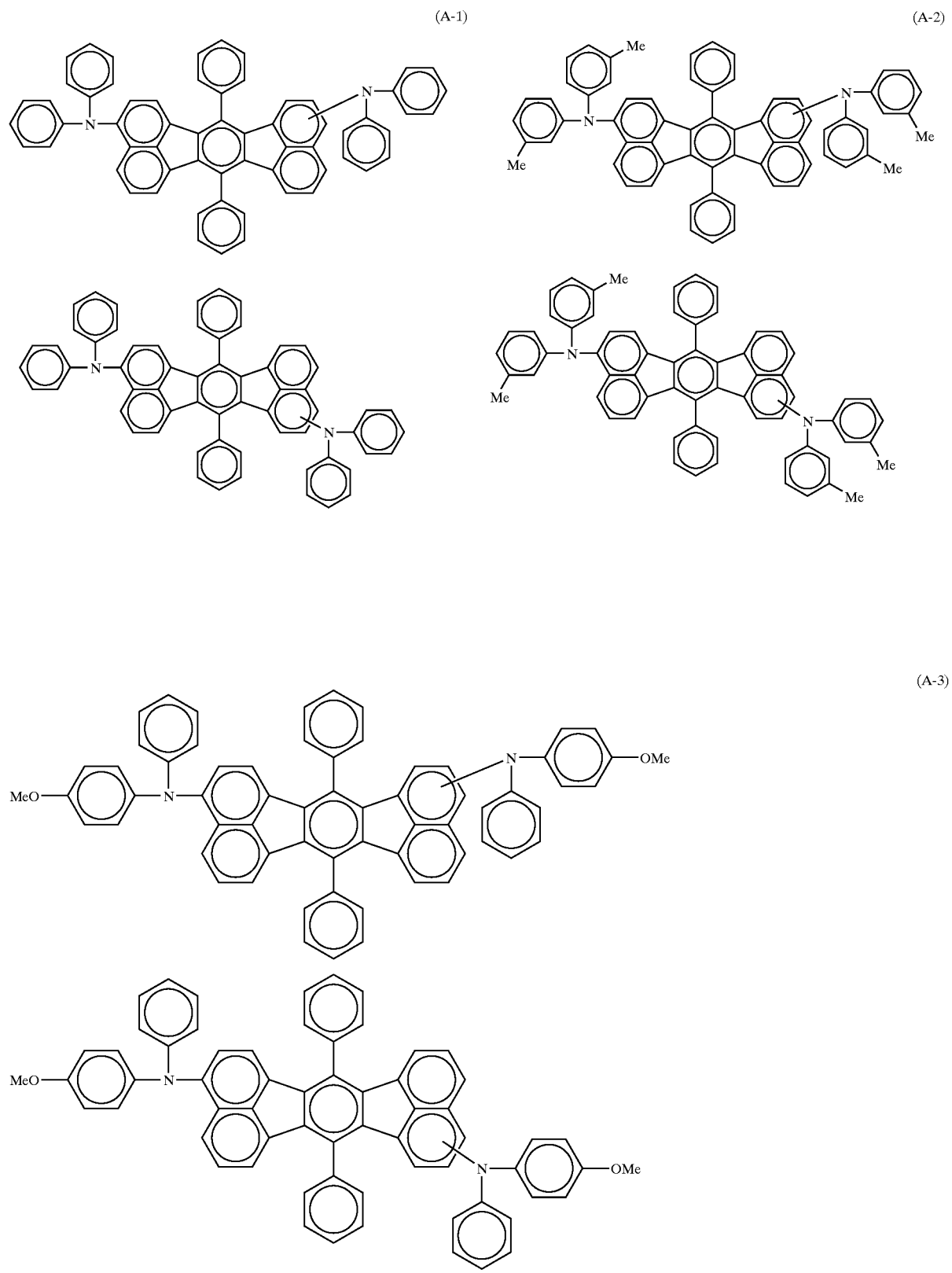

-continued
(A-4)
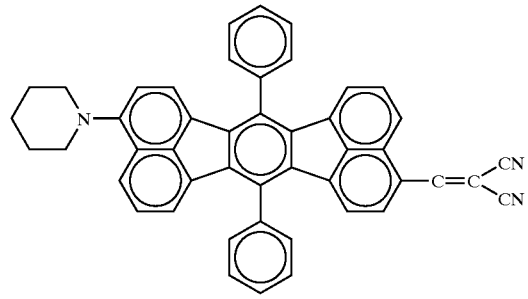
(A-5)
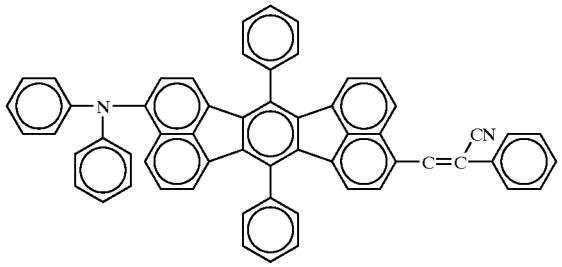
(A-6)
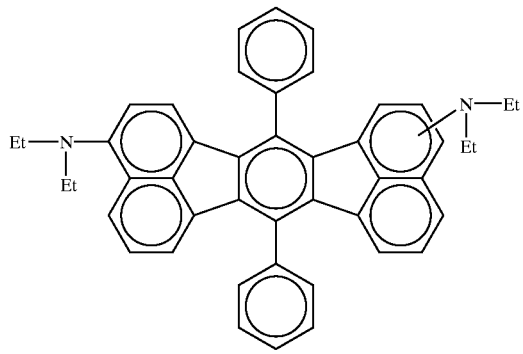
(A-7)
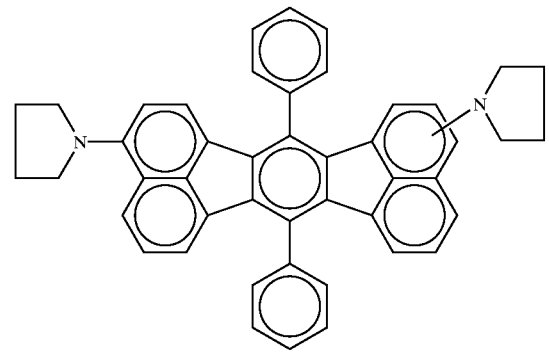
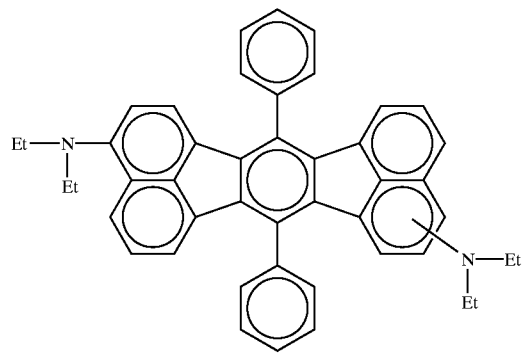
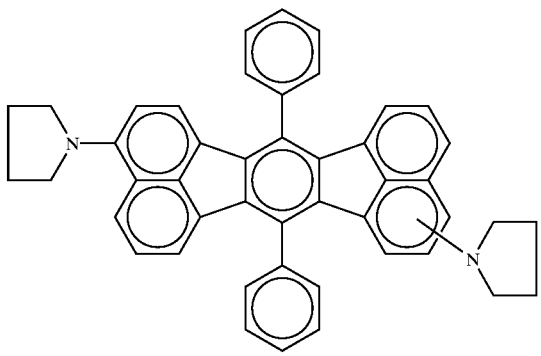

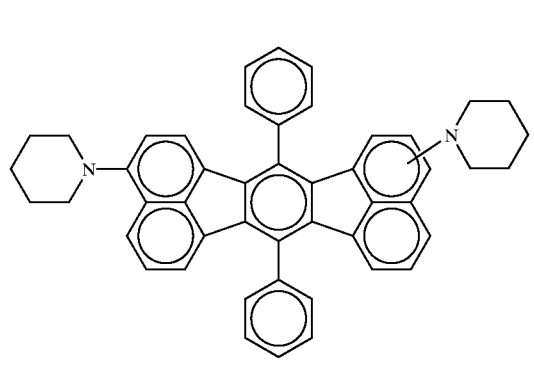
(A-8)
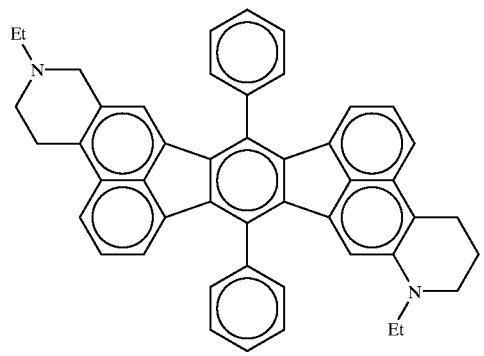
(A-9)
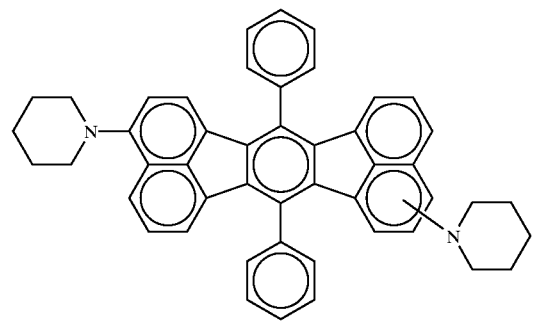
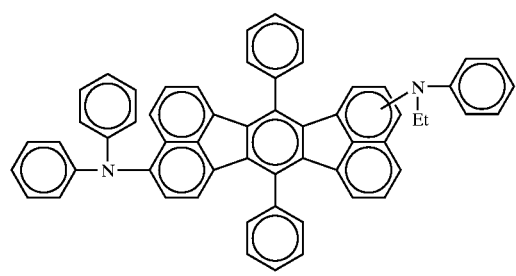
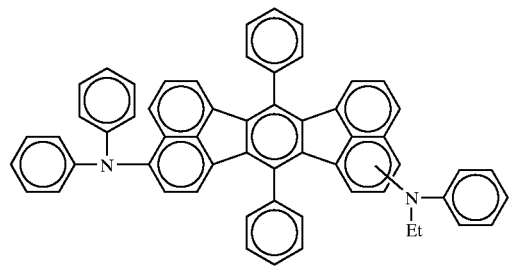
(A-10)

-continued
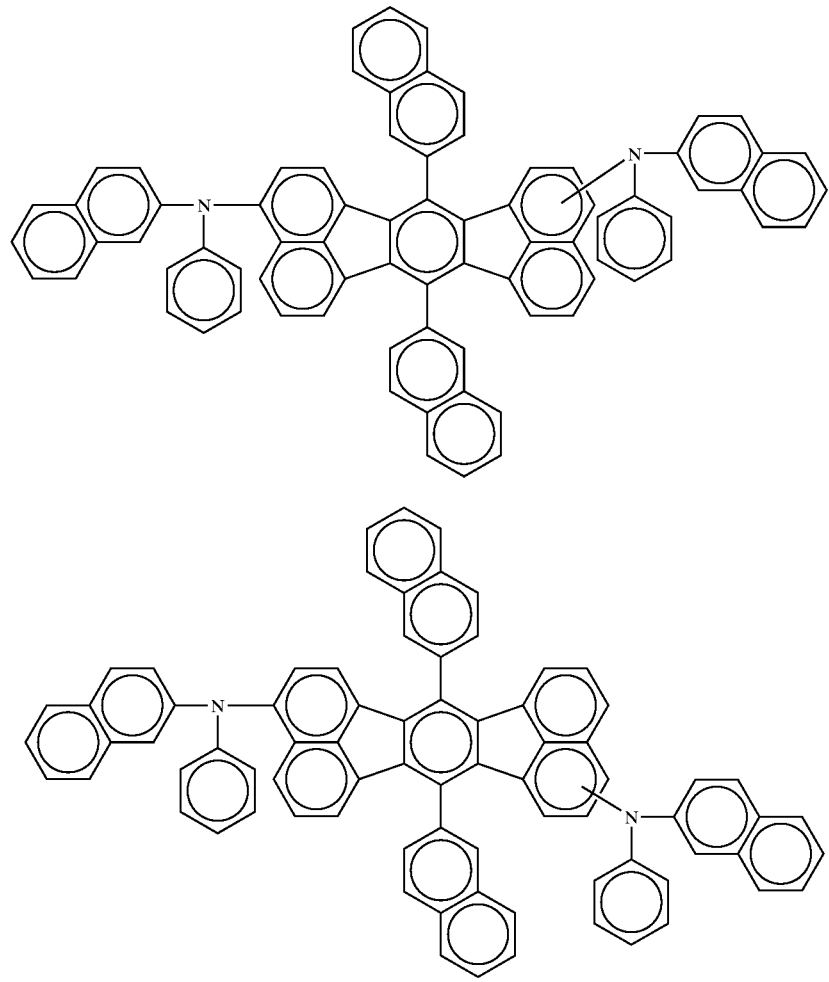
(A-11)
(A-11 continued / A-12 layout)
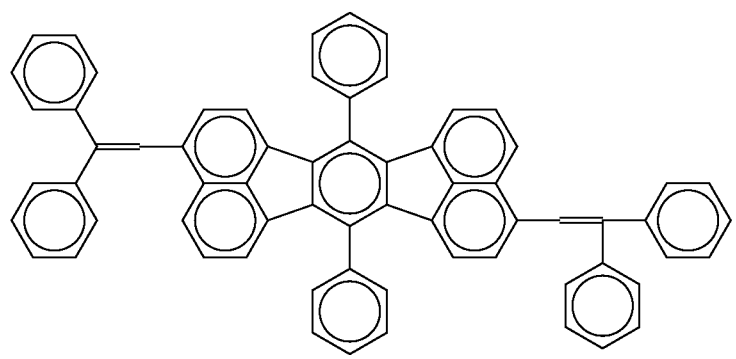
(A-12)

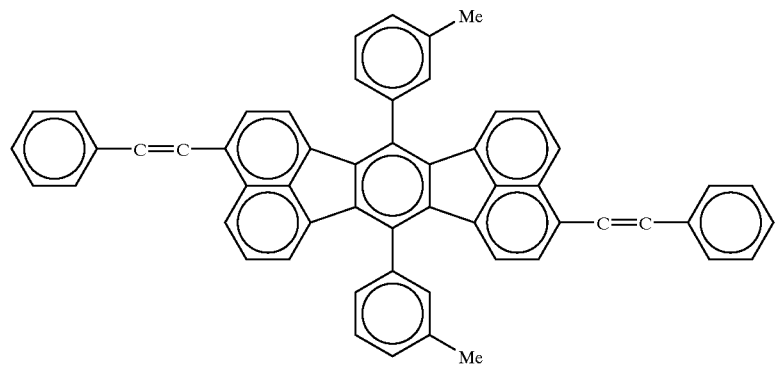
(A-13)
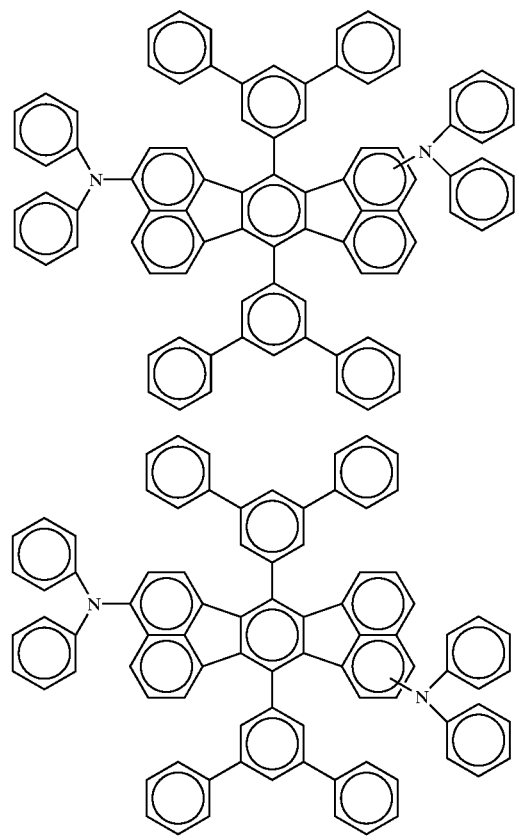
(A-14)
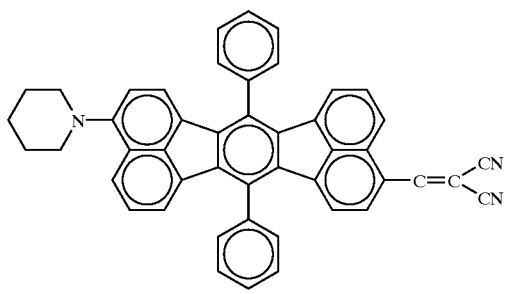
(A-15)

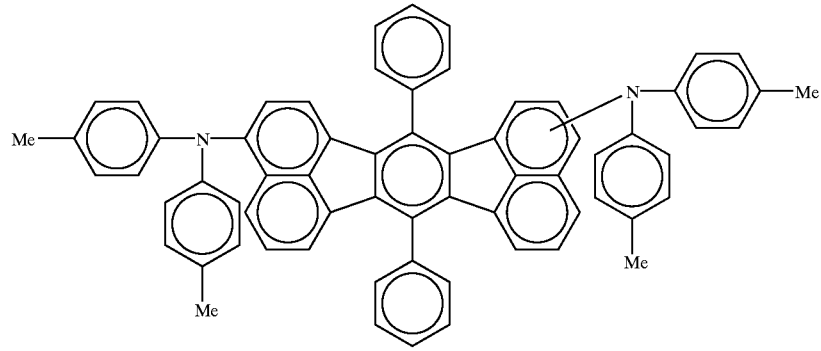
(A-16)
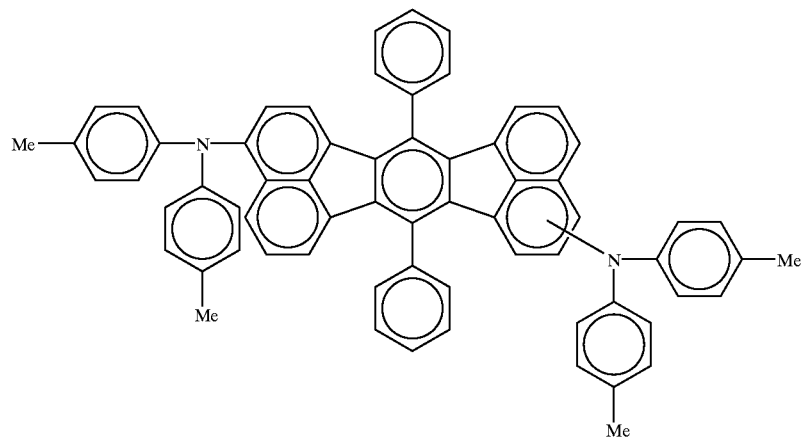
(A-17)
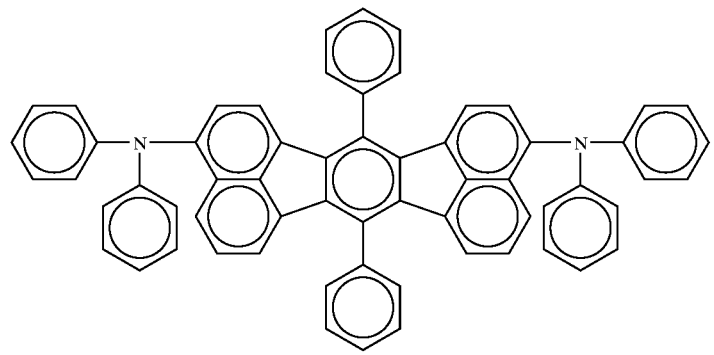
(A-18)
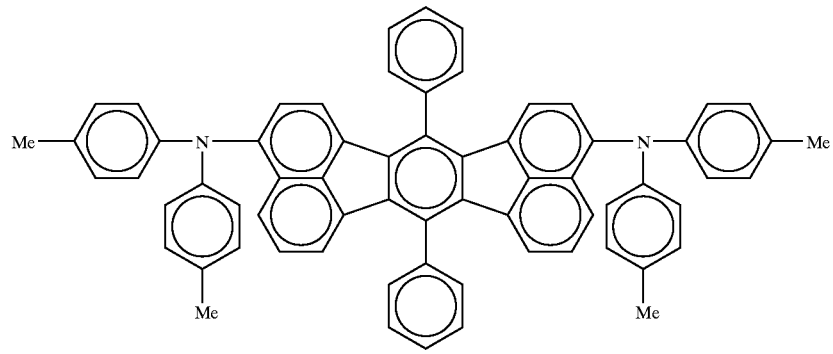

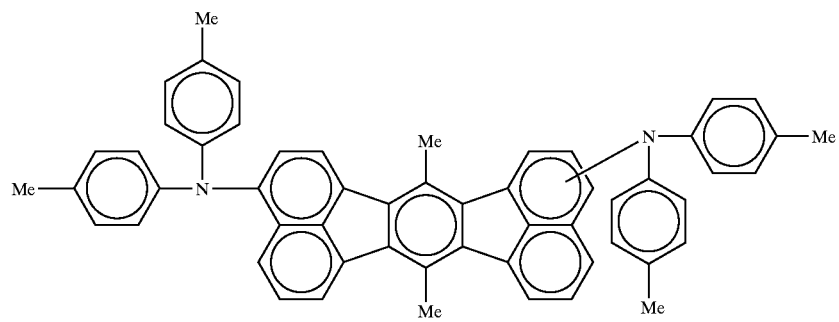
(A-19)
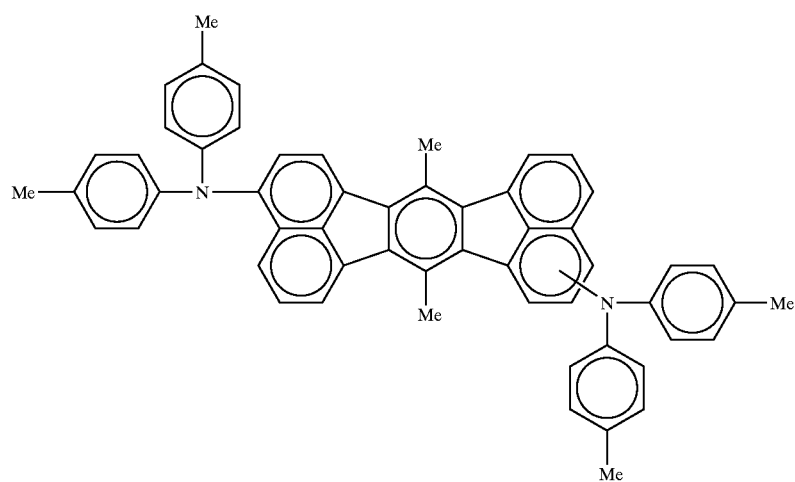
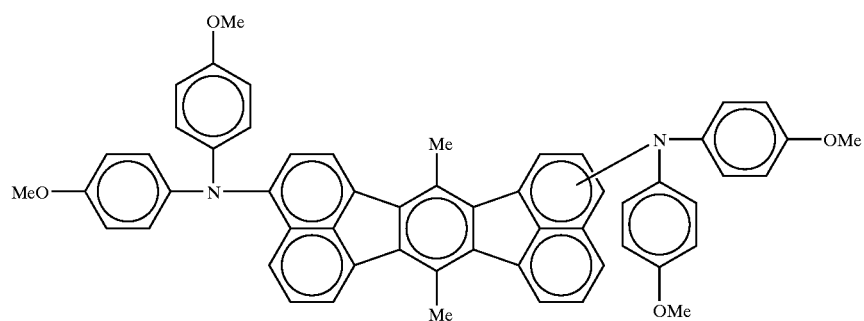
(A-20)
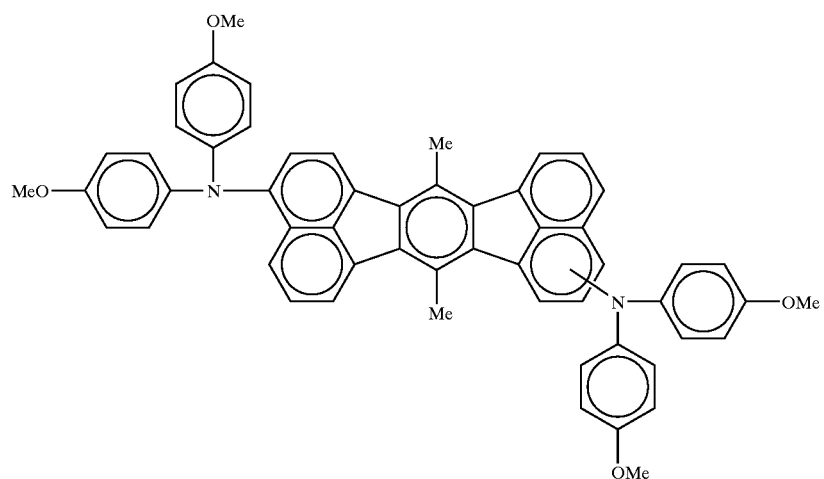

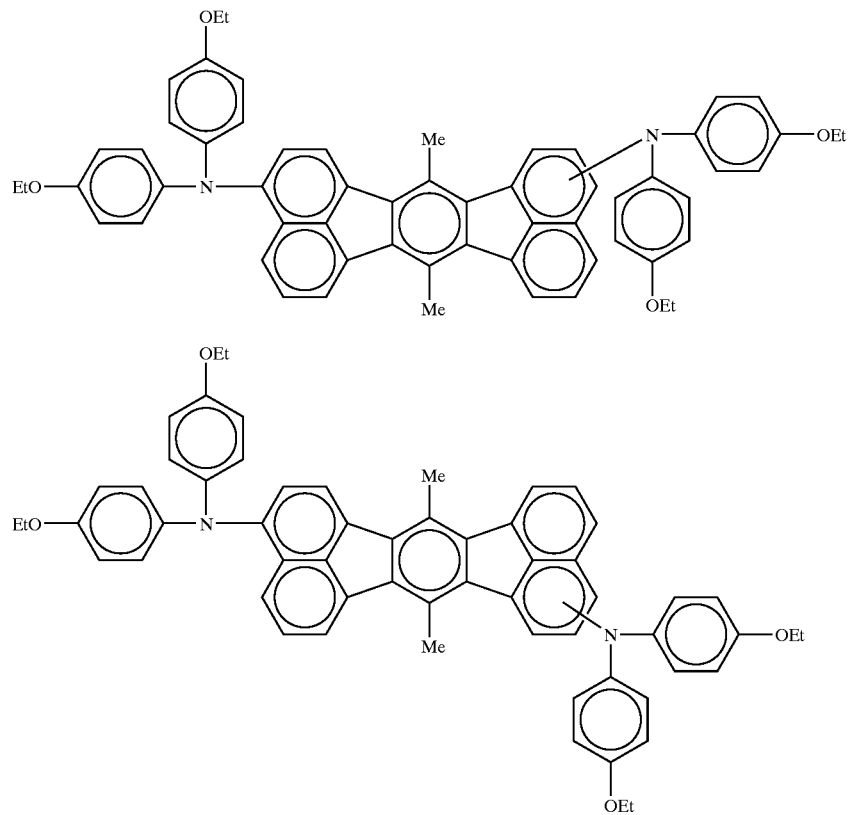
(A-21)
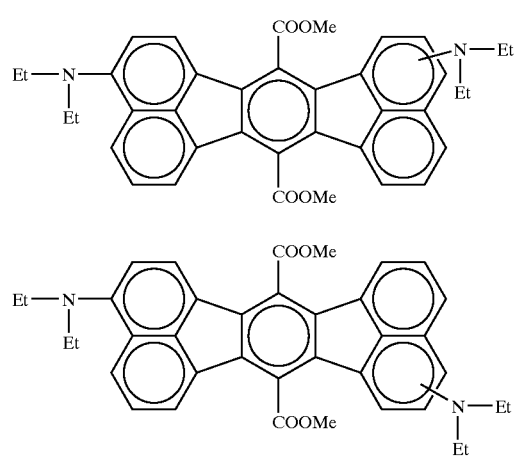
(A-22)
(A-23)

(A-24)
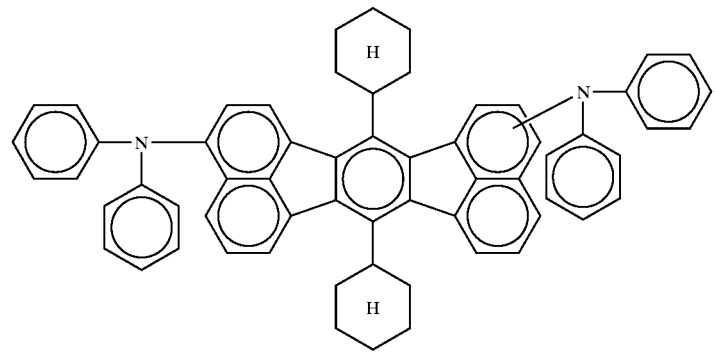
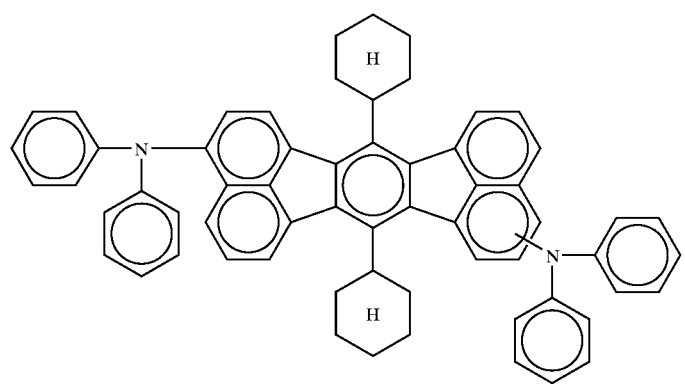
(A-25)
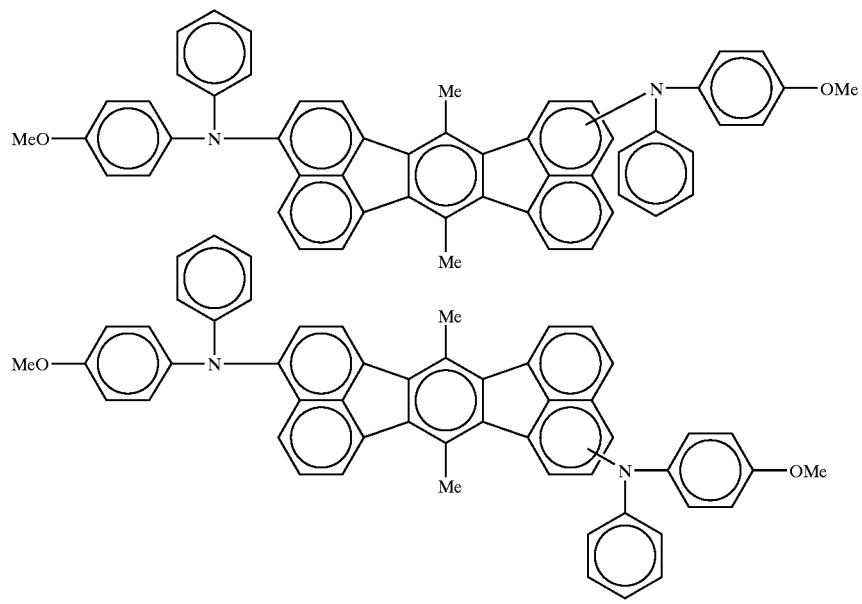

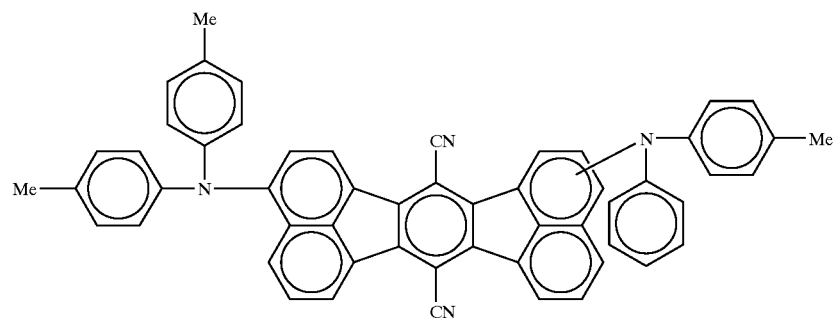
(A-26)
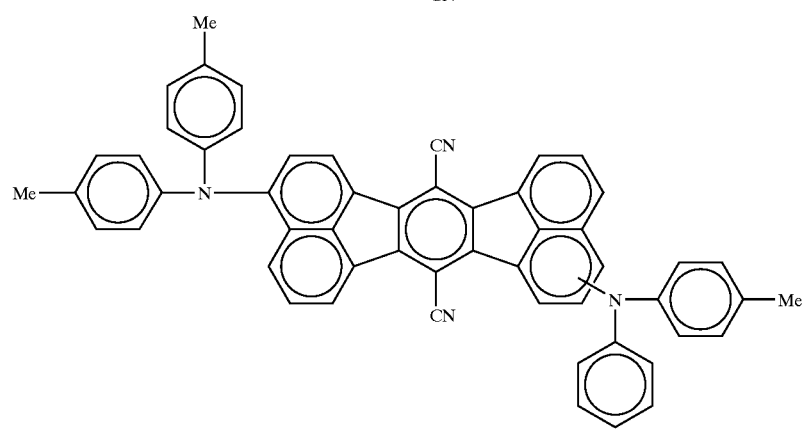
(A-27)
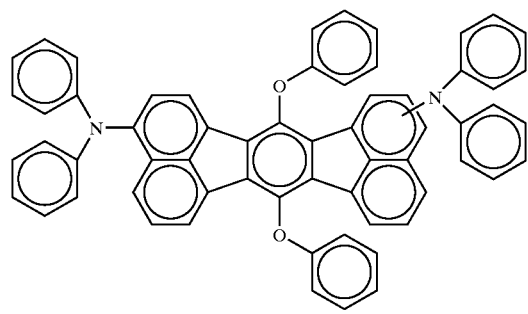
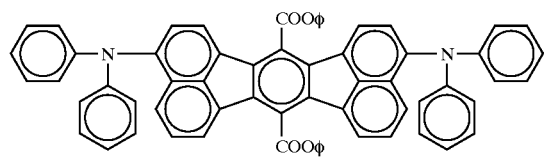
(A-28)
(φ is phenyl group)
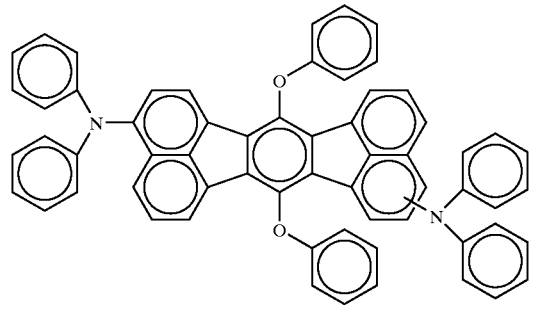
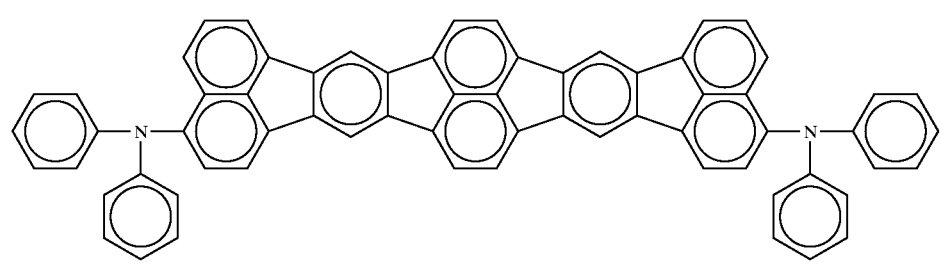
(B-1)

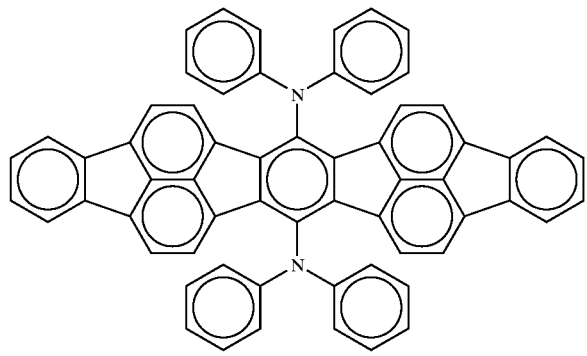
(B-2)
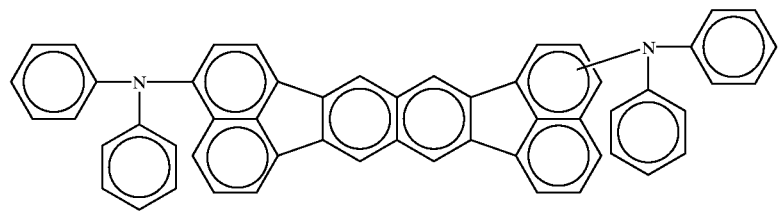
(B-3)
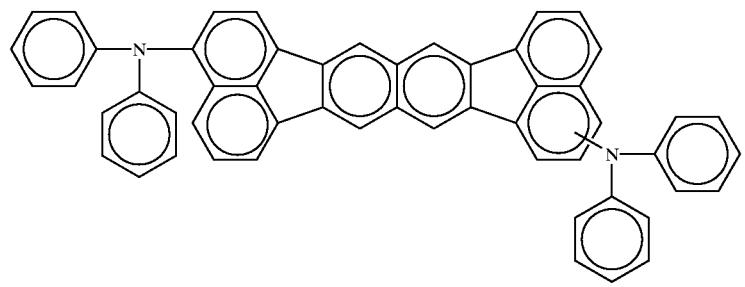
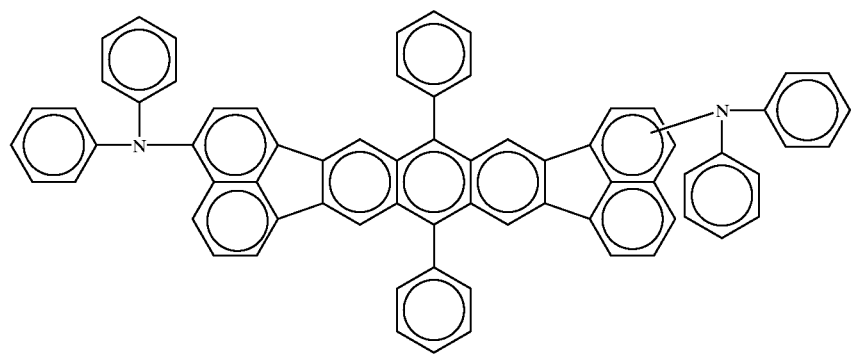
(B-4)
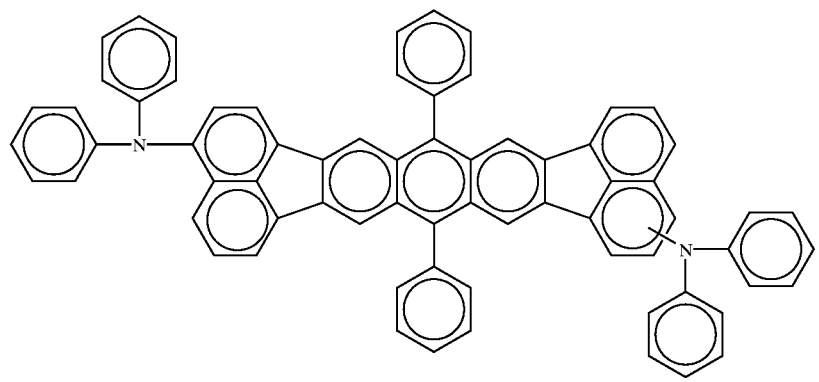

-continued
(B-5)
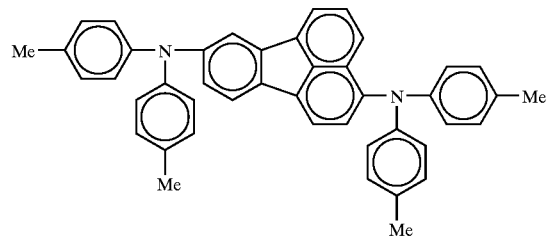
(B-6)
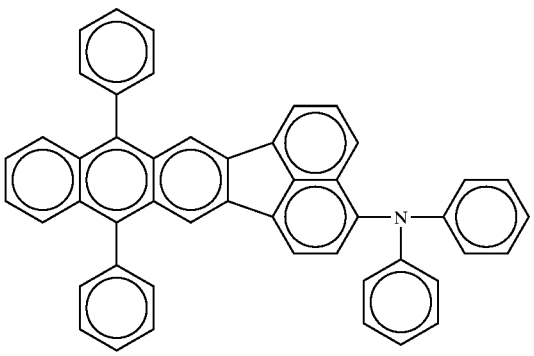
(B-7)
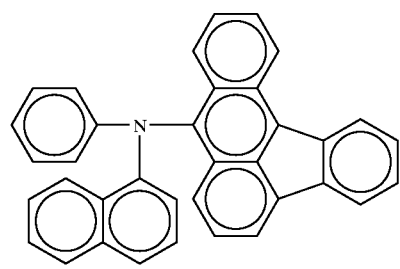
(B-8)
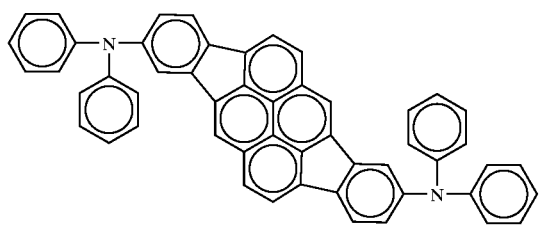
(B-9)
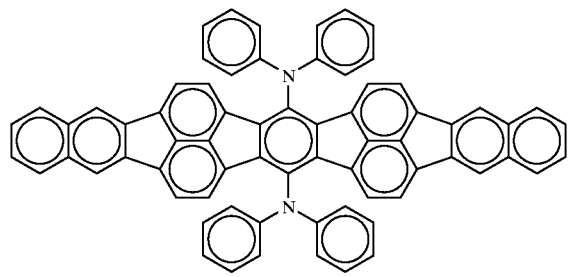
(B-10)
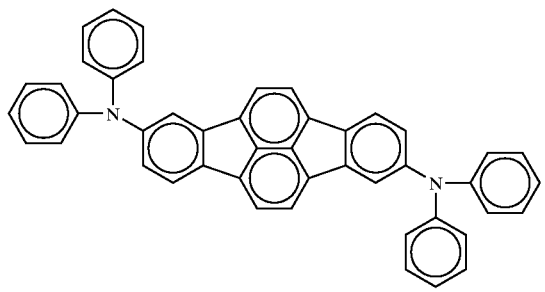
(B-11)
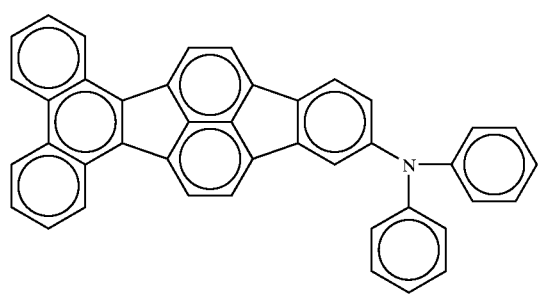
(B-12)
(B-13)
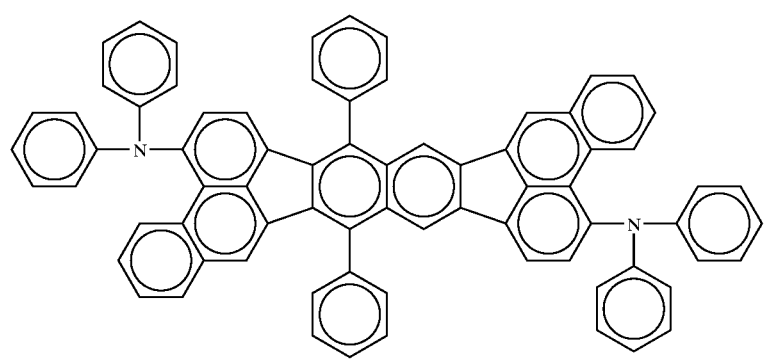

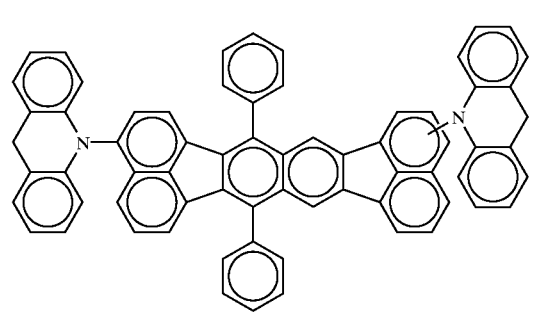 (B-14)
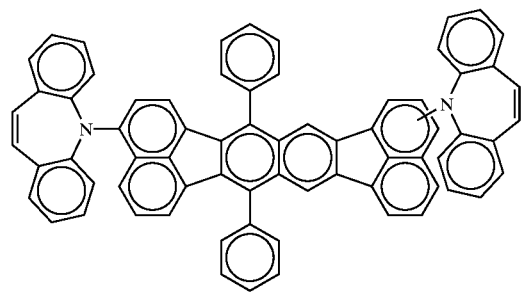 (B-15)
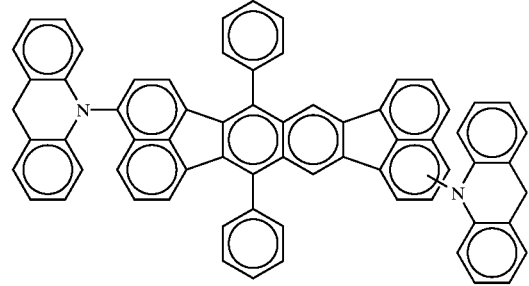
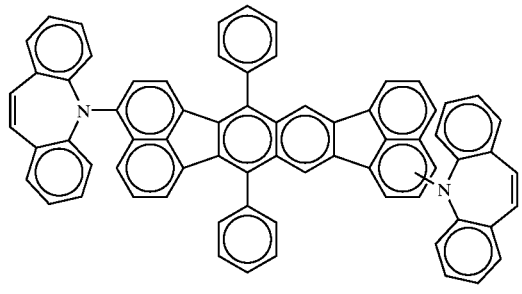
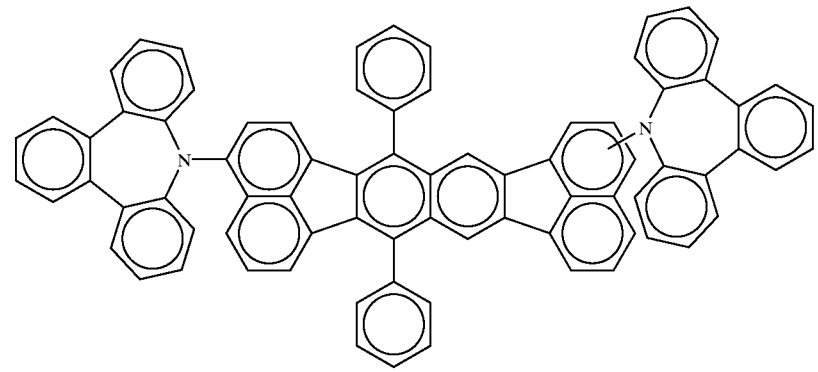 (B-16)
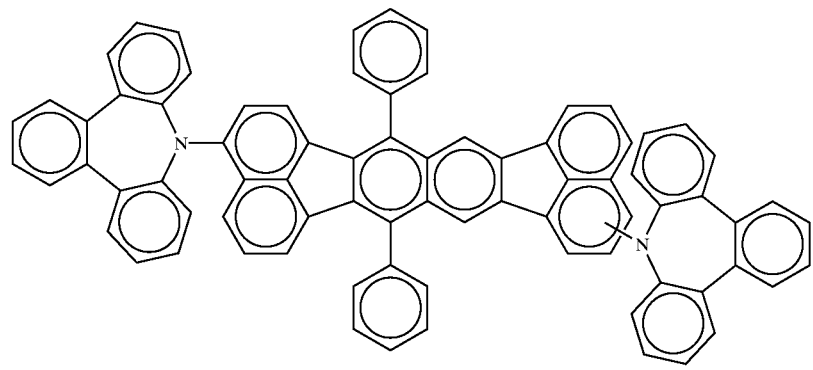

-continued

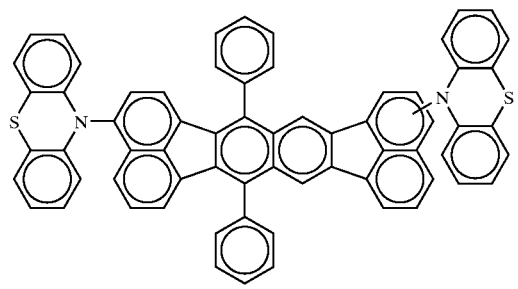
(B-17)

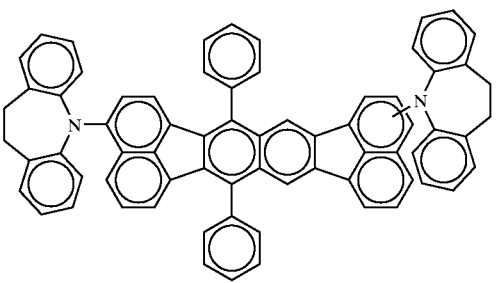
(B-18)

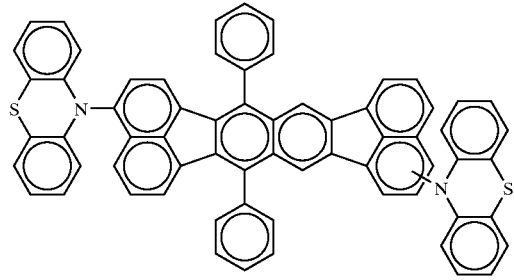

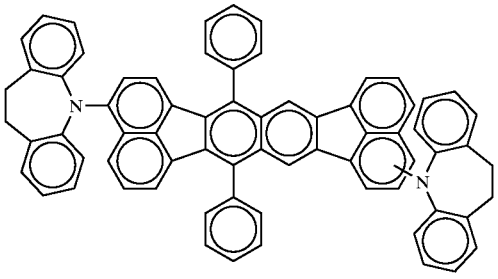

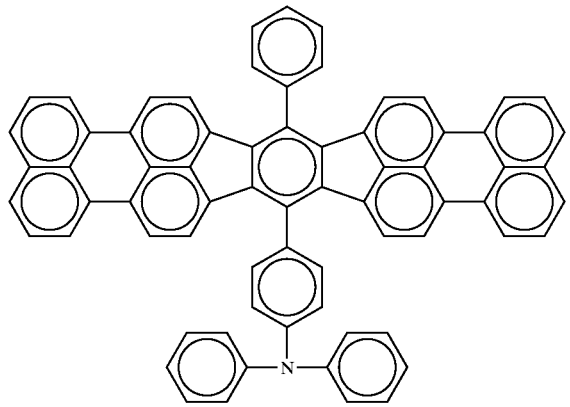
(B-19)

Since the compound used for the organic EL device of the present invention has the fluoranthene skeleton structure substituted with an amine group or an alkenyl group, the compound exhibits a high yield of fluorescence and emits reddish or yellowish light. Therefore, the organic EL device using this compound emits reddish to yellowish light, exhibits a high efficiency of light emission and has a long life.

The organic EL device of the present invention is a device in which one or a plurality of organic thin films are disposed between an anode and a cathode. When the device has a single organic layer, a light emitting layer is disposed between an anode and a cathode. The light emitting layer contains a light emitting material and may also contain a hole injecting material to transport holes injected at the anode to the light emitting material or an electron injecting material to transport electrons injected at the cathode to the light emitting material. It is preferable that the light emitting layer is formed with a light emitting material having a very high quantum efficiency of fluorescence emission and excellent ability to transfer holes and electrons and a uniform thin film is formed. The organic EL device having a multi-layer structure has a laminate structure such as: (an anode/a hole injecting layer/a light emitting layer/a cathode), (an anode/a light emitting layer/an electron injecting layer/a cathode) and (an anode/a hole injecting layer/a light emitting layer/an electron injecting layer/a cathode).

In the light emitting layer, where necessary, conventional light emitting materials, doping materials, hole injecting materials and electron injecting materials may be used in addition to the compound represented by any of general formulae [1] to [18] of the present invention. It is preferable that these compounds are added to any of the light emitting layer, the electron injecting layer, the hole transporting layer or the hole injecting layer in a concentration of 1 to 70% by weight and more preferably in a concentration of 1 to 20% by weight. In particular, it is preferable that the compound of the present invention is used as the doping material.

Deterioration in the luminance and the life caused by quenching can be prevented by the multi-layer structure of the organic EL. Where necessary, light emitting materials, other doping materials, hole injecting materials and electron injecting materials may be used in combination. By using other doping materials, the luminance and the efficiency of light emission can be improved and red light and white light can be emitted. The hole injecting layer, the light emitting layer and the electron injecting layer may each have a multi-layer structure having two or more layers. When the hole injecting layer has a multi-layer structure, the layer into which holes are injected from the electrode is referred to as the hole injecting layer and the layer which receives holes from the hole injecting layer and transports holes from the hole injecting layer to the light emitting layer is referred to as the hole transporting layer. When the electron injecting layer has a multi-layer structure, the layer into which electrons are injected from the electrode is referred to as the electron injecting layer and the layer which receives electrons from the electron injecting layer and transports electrons from the electron injecting layer to the light emitting layer is referred to as the electron transporting layer. These layers are each selected and used in accordance with factors such as the energy level, heat resistance and adhesion with the organic layers or the metal electrodes of the material.

Examples of the material which can be used in the organic layer as the light emitting material or the host material in combination with the compound represented by any of general formulae [1] to [18] include anthracene, naphthalene, phenanthrene, pyrene, tetracene, coronene, chrysene, fluoresceine, perylene, phthaloperylene, naphthaloperylene, perynone, phthaloperynone, naphthaloperynone, diphenylbutadiene, tetraphenylbutadiene, coumarine, oxadiazole, aldazine, bisbenzoxazoline, bisstyryl, pyrazine, cyclopentadiene, metal complexes of quinoline, metal complexes of aminoquinoline, metal complexes of benzoquinoline, imines, diphenylethylene, vinylanthracene, diaminocarbazole, pyrane, thiopyrane, polymethine, merocyanine, chelates of oxinoid compounds with imidazoles, quinacridone, rubrene, stilbene derivatives and fluorescent pigments. However, the above material is not limited to the compounds described above as the examples.

As the hole injecting material, a compound which has the ability to transfer holes, exhibits an excellent effect of hole injection from the anode and an excellent effect of hole injection to the light emitting layer or the light emitting material, prevents transfer of excited components formed in the light emitting layer into the electron injecting layer or the electron injecting material and has excellent ability to form a thin film is preferable. Examples of the above compound include phthalocyanine derivatives, naphthalocyanine derivatives, porphyrin derivatives, oxazole, oxadiazole, triazole, imidazole, imidazolone, imdazolethione, pyrazoline, pyrazolone, tetrahydroimidazole, oxazole, oxadiazole, hydrazone, acylhydrazone, polyarylalkanes, stilbene, butadiene, triphenylamines of the benzidine-type, triphenylamines of the styrylamine type, triphenylamines of the diamine type, derivatives of these compounds and macromolecular compounds such as polyvinylcarbazole, polysilane and conductive macromolecules. However, the above compound is not limited to the compounds described above as the examples.

Among the hole injection materials which can be used in the organic EL device of the present invention, aromatic tertiary amine derivatives and phthalocyanine derivatives are more effective.

Examples of the aromatic tertiary amine derivative include triphenylamine, tritolylamine, tolyldiphenylamine, N,N'-diphenyl-N,N'-(3-methylphenyl)-1,1'-biphenyl-4,4'-diamine, N,N,N',N'-(4-methylphenyl)-1,1'-phenyl-4,4'-diamine, N,N,N',N'-(4-methylphenyl)-1,1'-biphenyl-4,4'-diamine, N,N'-diphenyl-N,N'-dinaphthyl-1,1'-biphenyl-4,4'-diamine, N,N'-(methylphenyl)-N,N'-(4-n-butylphenyl) phenanthrene-9,10-diamine, N,N-bis(4-di-4-tolylaminophenyl)-4-phenylcyclohexane and oligomers and polymers having a skeleton structure of these aromatic tertiary amines. However, the aromatic tertiary amine derivative is not limited to the compounds described above as the examples.

Examples of the phthalocyanine (Pc) derivative include $H_2Pc$, CuPc, CoPc, NiPc, ZnPc, PdPc, FePc, MnPc, ClAlPc, ClGaPc, ClInPc, ClSnPc, $Cl_2SiPc$, (HO)AlPc, (HO)GaPc, VOPc, TiOPc, MoOPc, GaPc-O-GaPc and corresponding derivatives of naphthalocyanine. However, the derivatives of phthalocyanine and naphthalocyanine are not limited to the compounds described above as the examples.

As the electron injecting material, a compound which has the ability to transport electrons, exhibits an excellent effect of electron injection from the cathode and an excellent effect of electron injection to the light emitting layer or the light emitting material, prevents transfer of excited components formed in the light emitting layer into the hole injecting layer and has excellent ability to form a thin film is preferable. Examples of the above compound include fluorenone, anthraquinodimethane, diphenoquinone, thiopyrane dioxide, oxazole, oxadiazole, triazole, imidazole, perylene-teteracarboxylic acid, fluorenylidenemethane, anthraquinodimethane, anthrone and derivatives of these compounds. However, the above compound is not limited to the compounds described above as the examples. The charge injecting property can be improved by adding an electron accepting material to the hole injecting material or by adding an electron donating material to the electron injecting material.

In the organic EL device of the present invention, more effective electron injecting materials are metal complex compounds and five-membered derivatives containing nitrogen.

Examples of the metal complex compound include 8-hydroxy-quinolinatolithium, bis(8-hydroxyquinolinato) zinc, bis(8-hydroxy-quinolinato)copper, bis(8-hydroxyquinolinato)manganese, tris(8-hydroxy-quinolinato)aluminum, tris(2-methyl-8-hydroxyquinolinato) aluminum, tris(8-hydroxyquinilinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum and bis(2-methyl-8-quinolinato)(2-naphtholato)gallium. However, the metal complex compound is not limited to the compounds described above as the examples.

Preferable examples of the five-membered derivative containing nitrogen include derivatives of oxazoles, thiazoles, thiadiazoles and triazoles. Specific examples include 2,5-bis (1-phenyl)-1,3,4-oxazole, dimethylPOPOP, 2,5-bis(1-phenyl)-1,3,4-thiazole, 2,5-bis(1-phenyl)-1,3,4-oxadiazole, 2-(4'-tert-butylphenyl)-5-(4"-biphenyl)-1,3,4-oxadiazole, 2,5-bis(1-naphthyl)-1,3,4-oxadiazole, 1,4-bis[2-(5-phenyloxadiazolyl)]benzene, 1,4-bis[2-(5-phenyloxadiazolyl)-4-tert-butylbenzene], 2-(4'-tert-butylphenyl)-5-(4"-biphenyl)-1,3,4-thiadiazole, 2,5-bis(1-naphthyl)-1,3,4-thiadiazole, 1,4-bis[2-(5-phenylthiadiazolyl)]benzene, 2-(4'tert-butylphenyl)-5-(4"-biphenyl)-1,3,4-triazole, 2,5-bis(1-naphthyl)-1,3,4-triazole and 1,4-bis[2-(5-phenyltriazolyl)]benzene. However, the five-membered derivative containing nitrogen is not limited to the compounds described above as the examples.

In the organic EL device of the present invention, the organic layer may contain at least one of light emitting materials, doping materials, hole injecting materials and electron injecting materials in the same layer in addition to the compound represented by any of general formulae [1] to [18]. In order to improve stability of the organic EL device of the present invention with respect to the temperature, the humidity and the atmosphere, a protecting layer may be formed on the surface of the device or the entire device may be protected with silicon oil or a resin.

As the conductive material used for the anode of the organic EL device, a material having a work function of 4 eV or greater is suitable. Examples of such a material include carbon, aluminum, vanadium, iron, cobalt, nickel, tungsten, silver, gold, platinum, palladium, alloys of these metals, metal oxides used for ITO substrates and NESA substrates such as tin oxide and indium oxide and organic conductive resins such as polythiophene and polypyrrol. As the conductive material used for the cathode, a material having a work function smaller than 4 eV is suitable. Examples of such a material include magnesium, calcium, tin, lead, titanium, yttrium, lithium, ruthenium, manganese, aluminum and alloys of these metals. However, the materials used for the anode and the cathode are not limited to the materials described above as the examples. Typical examples of the alloy include alloys of magnesium and silver, alloys of magnesium and indium and alloys of lithium and aluminum. However, the alloy is not limited to these alloys described as the examples. The composition of the alloy is controlled by the temperature of the source of vapor deposition, the atmosphere and the degree of vacuum and can be adjusted suitably. The anode and the cathode may have a multi-layer structure having two or more layers, where necessary.

In the organic EL device of the present invention, it is preferable that a layer of a chalcogenide, a metal halide or a metal oxide (this layer may occasionally be referred to as a surface layer) is disposed on the surface of at least one of the pair of electrodes prepared as described above. Specifically, it is preferable that a layer of a chalcogenide (including an oxide) of a metal such as silicon and aluminum is disposed on the surface of the anode at the side of the layer of the light emitting medium and a layer of a metal halide or a metal oxide is disposed on the surface of the cathode at the side of the layer of the light emitting medium. Due to the above layers, stability in driving can be improved.

Preferable examples of the chalcogenide include $SiO_x$ ($1 \leq x \leq 2$), $AlO_x$ ($1 \leq x \leq 1.5$), SiON and SiAlON. Preferable examples of the metal halide include LiF, $MgF_2$, $CaF_2$ and fluorides of rare earth metals. Preferable examples of the metal oxide include $Cs_2O$, $Li_2O$, MgO, SrO, BaO and CaO.

In the organic EL device of the present invention, it is preferable that a mixed region of an electron transmitting compound and a reducing dopant or a mixed region of a hole transmitting compound and an oxidizing dopant is disposed on the surface of at least one of the pair of electrodes prepared as described above. Due to the mixed region disposed on the surface of the pair of electrodes, the electron transmitting compound is reduced to form an anion and injection and transportation of electrons from the mixed region into the light emitting medium can be facilitated. The hole transmitting compound is oxidized to form a cation and injection and transportation of holes from the mixed region into the light emitting medium is facilitated. Preferable examples of the oxidizing dopant include various types of Lewis acid and acceptor compounds. Preferable examples of the reducing dopant include alkali metals, compounds of alkali metals, alkaline earth metals, rare earth metals and compounds of these metals.

In the organic EL device, to achieve efficient light emission, it is preferable that at least one face of the device is sufficiently transparent in the wave length region of the emitted light. It is preferable that the substrate is also transparent. The transparent electrode is disposed in accordance with vapor deposition or sputtering using the above conductive material in a manner such that the prescribed transparency is surly obtained. It is preferable that the electrode disposed on the light emitting face has a transmittance of light of 10% or greater. The substrate is not particularly limited as long as the substrate has sufficient mechanical strength and strength at high temperatures and is transparent. Glass substrates or transparent films of resins may be used. Example of the transparent films of resins include films of polyethylene, ethylene-vinyl acetate copolymers, ethylene-vinyl alcohol copolymers, polypropylene, polystyrene, polymethyl methacrylate, polyvinyl chloride, polyvinyl alcohol, polyvinyl butyral, nylon, polyether ether ketones, polsulfones, polyether sulfones, tetrafluoroethylene-perfluoroalkyl vinyl ether copolymers, polyvinyl fluoride, tetrafluoroethylene-ethylene copolymers, tetrafluoroethylene-hexafluoropropylene copolymers, polychlorotrifluoro-ethylene, polyvinylidene fluoride, polyesters, polycarbonates, polyurethanes, polyimides, polyether imides, polyimides and polypropylene.

Each layer of the organic EL device of the present invention can be formed suitably in accordance with a dry process of film formation such as vacuum vapor deposition, sputtering, plasma plating and ion plating or a wet process of film formation such as spin coating, dipping and flow coating. The thickness of the film is not particularly limited. However, it is necessary that the thickness be set at a suitable value. When the thickness is greater than the suitable value, a high voltage must be applied to obtain a prescribed output of light and the efficiency decreases. When the thickness is smaller than the suitable value, pin holes are formed and a sufficient luminance cannot be obtained even when the electric field is applied. In general, the suitable range of the thickness is 5 nm to 10 $\mu$m. A thickness in the range of 10 nm to 0.2 $\mu$m is preferable.

When the device is produced in accordance with a wet process, materials forming each layer are dissolved or dispersed in a suitable solvent such as ethanol, chloroform, tetrahydrofuran and dioxane and a film is formed from the solution or the suspension. The solvent is not particularly limited. In any organic thin layer, suitable resins and additives may be used to improve the property to form a film and to prevent formation of pin holes. Examples of the resin which can be used include insulating resins such as polystyrene, polycarbonates, polyarylates, polyesters, polyamides, polyurethanes, polysulfones, polymethyl methacrylate, polymethyl acrylate and cellulose, copolymers derived from these resins, photoconductive resins such as poly-N-vinylcarbazole and polysilane and conductive resins such as polythiophene and polypyrrol. Examples of the additive include antioxidants, ultraviolet light absorbents and plasticizers.

As described above, when the compound of the present invention is used for the organic layer of the organic EL device, the organic EL device exhibiting an excellent purity of color and a high efficiency of light emission, having a long life and emitting red light can be obtained.

The organic EL device of the present invention can be used for a planar light emitting member such as a flat panel display of wall televisions, a back light for copiers, printers and liquid crystal displays, a light source of instruments, display panels and a marker light.

The present invention will be described more specifically with reference to Synthesis Examples and Examples in the following.

SYNTHESIS EXAMPLE 1 (COMPOUND A-1)

3,10- and 3,11-Bisdiphenylamino-7,14-diphenylacenaphtho[1,2-k]fluoranthene was synthesized via the reaction route shown in the following:

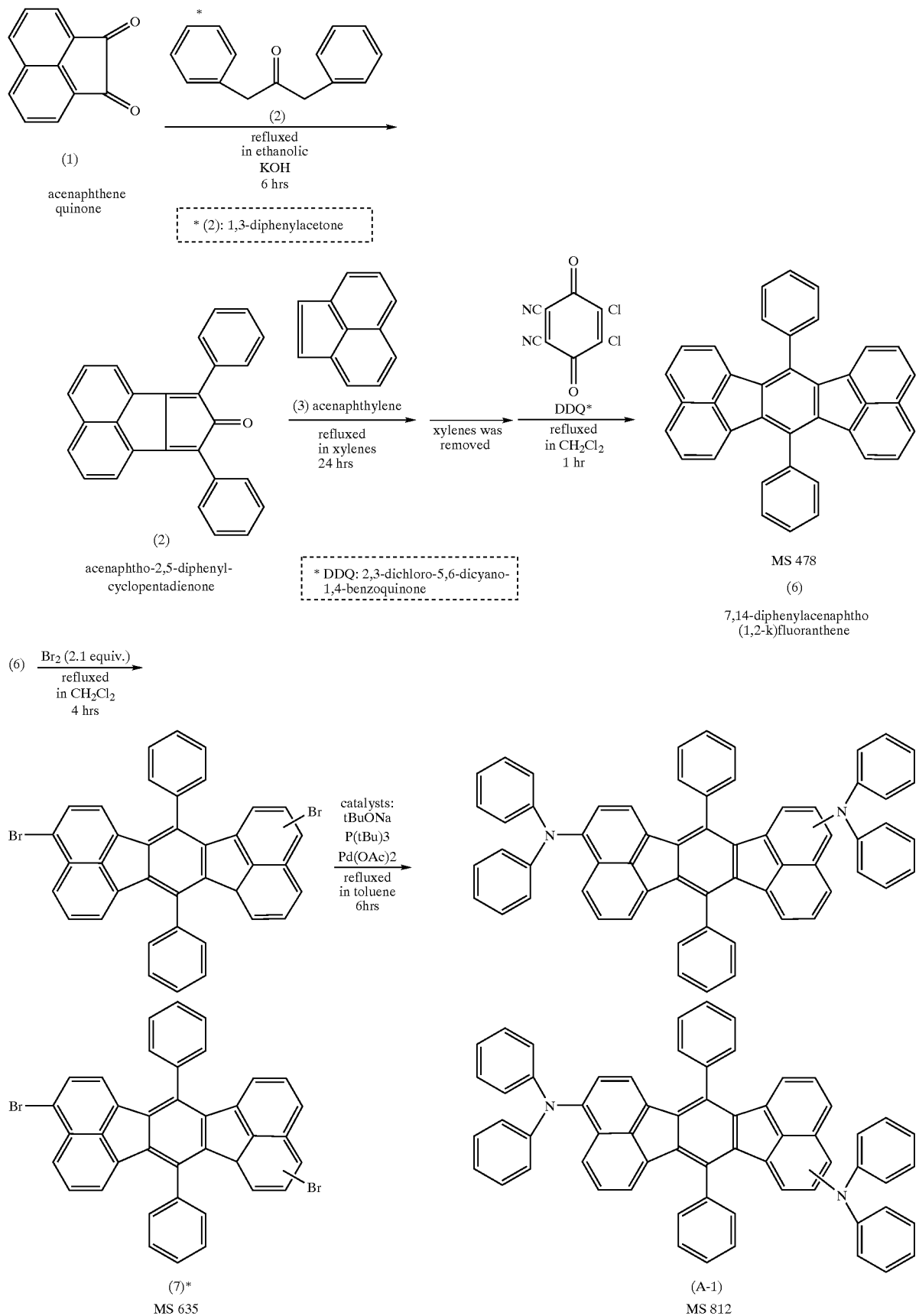

* (1) ⟶ (7)

cf. Jeff. D. Debad, Allen J. Bard J. Am. Chem. Soc, vol.120 2476 (1998).

(A) Synthesis of 3,10- and 3,11-dibromo-7,14-diphenylacenaphtho[1,2-k]fluoranthenes In accordance with the J. B. Allen's process, 3,10- and 3,11-dibromo-7,14-diphenylacenaphtho[1,2-k]fluoranthenes (7) were synthesized using acenaphthenequinone (1) as the starting material via 7,14-diphenylacenaphtho[1,2-k]fluoranthene (6). The structures of 3,10- and 3,11-dibromo-7,14-diphenylacenaphtho[1,2-k]fluoranthenes were identified from FD-MS (the field desorption mass spectra) and the $^1$H-NMR spectra. The chemical shifts in $^1$H-NMR agreed with the measured values reported by Allen (J. D. Debad, A. I. Bard, J. Chem. Soc., Vol. 120, 2476 (1998)).

(B) Synthesis of 3,10- and 3,11-diphenylamino-7,14-diphenylacenaphthofluoranthenes (Compound A-1)

Into 150 ml of toluene, 3.56 g (5.6 mmole) of 3,10- and 3,11-dibromo-7,14-diphenylacenaphtho[1,2-k]fluoranthenes (7), 1.89 g (11.2 mmole) of diphenylamine, 0.06 g (0.3 mmole) of palladium acetate, 0.22 g (1.1 mmole) of tri-tert-butylphosphine and 1.51 g (14.0 mmole) of sodium tert-butoxide were dissolved at the room temperature and the reaction was allowed to proceed for 6 hours while the mixture was refluxed under heating. The resultant reaction mixture was filtered. The filtrate was concentrated and 4.8 g of a red orange powdery solid was obtained. After the solid was dissolved in toluene, the solution was fractionated in accordance with the column chromatography using a column packed with silica gel and 4.1 g of the main component was obtained. The main component was confirmed to be 3,10- and 3,11-diphenylamino-7,14-diphenylacenaphthofluoranthenes (Compound A-1) from FD-MS (812) and the structure of Compound (7). Precipitates in the reaction mixture separated by the filtration was washed with acetone and water and dried and 0.6 g of a powdery solid was obtained. The obtained solid was confirmed to have the same structure as that of the product obtained from the filtrate from FD-MS (812) and the $^1$H-NMR spectrum.

Similarly, Compound A-16 (Synthesis Example 2), Compound B-15 (Synthesis Example 3), Compound A-8 (Synthesis Example 4), Compound B-18 (Synthesis Example 5) and Compound B-17 (Synthesis Example 6) which are compounds of 3,10- and 3,11-diamino-7,14-diphenylacenaphtho[1,2-k]fluoranthenes were synthesized via the reaction routes shown in the following:

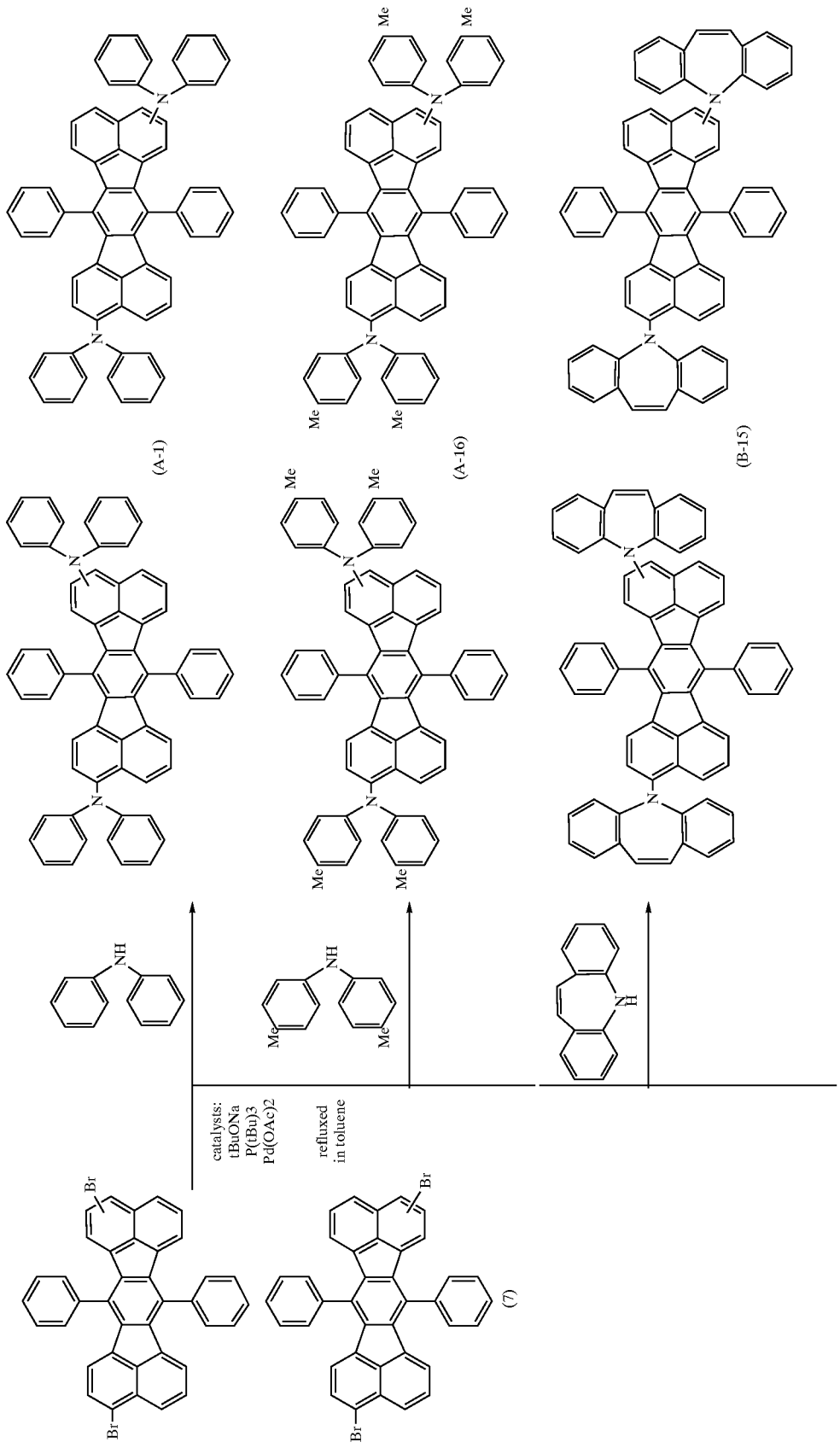

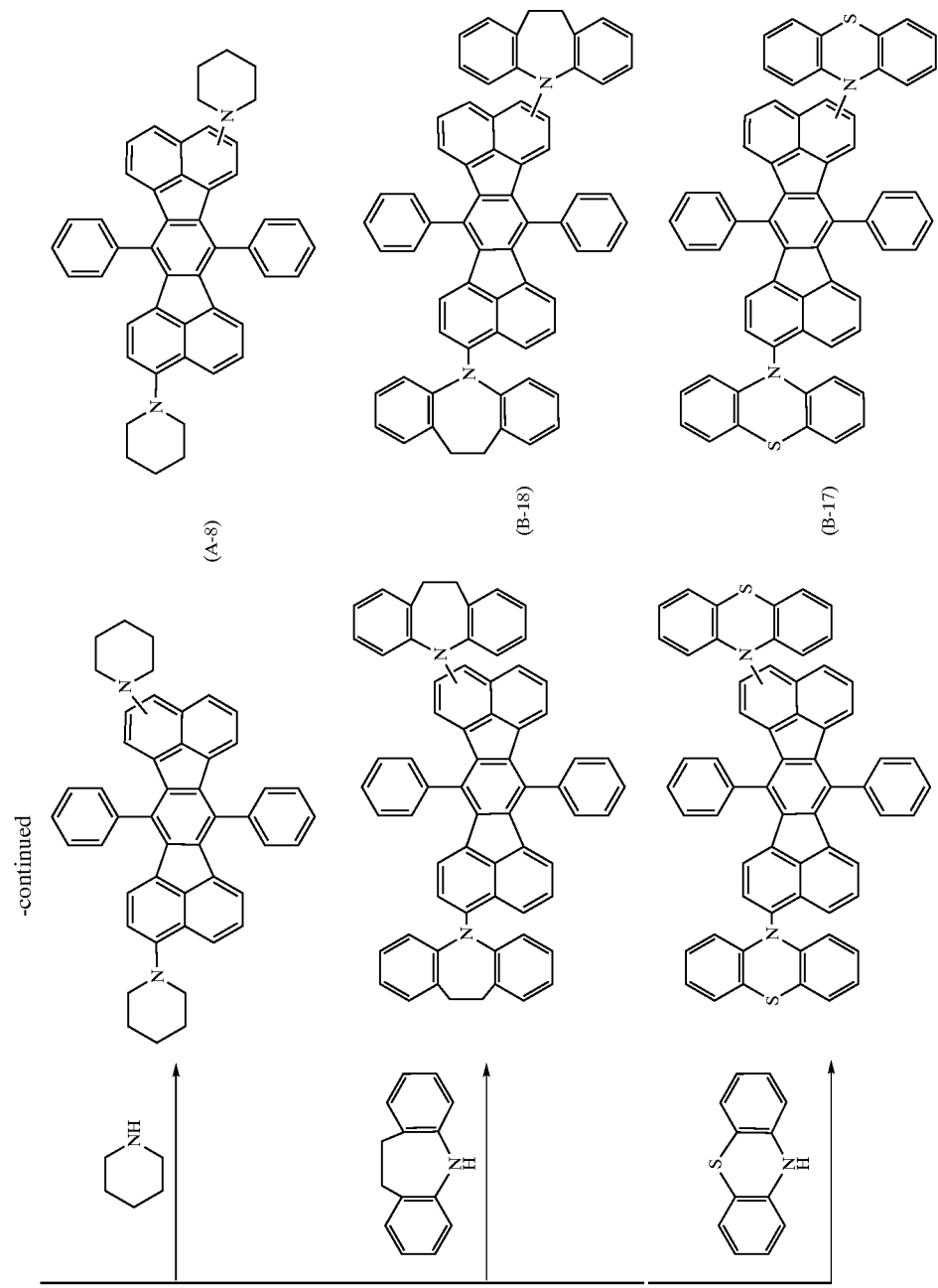

SYNTHESIS EXAMPLE 2 (COMPOUND A-16)

The reaction was conducted in accordance with the same procedures as those conducted in Synthesis Example 1 (B) except that 2.31 g (11.7 mmole) of p,p'-ditolylamine was used in place of diphenylamine. After the reaction was completed, the reaction mixture was filtered. The filtrate was washed with water and concentrated and a red powdery solid was obtained. The obtained solid was fractionated in accordance with the column chromatography using a column packed with silica gel and 2.9 g of the main component having a high purity was obtained. The main component was confirmed to be Compound A-16 from FD-MS (868).

SYNTHESIS EXAMPLE 3 (COMPOUND B-15)

The reaction was conducted in accordance with the same procedures as those conducted in Synthesis Example 1 (B) except that 2.27 g (11.7 mmole) of iminostilbene was used in place of diphenylamine. After the reaction was completed, the product precipitated in the reaction mixture was separated, repeatedly washed with acetone and water and dried and 3.4 g of a red orange powdery solid was obtained. The obtained solid was dissolved in tetrahydrofuran and fractionated in accordance with the thin layer chromatography using a thin layer of silica gel and 2.3 g of the main component having a high purity was obtained. The main component was confirmed to be Compound B-15 from FD-MS (862).

SYNTHESIS EXAMPLE 4 (COMPOUND A-8)

The reaction was conducted in accordance with the same procedures as those conducted in Synthesis Example 1 (B) except that 1.0 g (11.7 mmole) of piperidine was used in place of diphenylamine. After the reaction was completed, the reaction mixture was filtered. The filtrate was washed with water and concentrated and a red powdery solid was obtained. The obtained solid was dissolved in toluene and fractionated in accordance with the column chromatography using a column packed with silica gel and 2.1 g of the main component having a high purity was obtained. The main component was confirmed to be Compound A-8 from FD-MS (644).

SYNTHESIS EXAMPLE 5 (COMPOUND B-18)

The reaction was conducted in accordance with the same procedures as those conducted in Synthesis Example 1 (B) except that 1.96 g (11.7 mmole) of carbazole was used in place of diphenylamine. After the reaction was completed, the product precipitated in the reaction mixture was separated, repeatedly washed with acetone and water and dried and 3.8 g of a red orange powdery solid was obtained. The obtained solid was dissolved in tetrahydrofuran and fractionated in accordance with the thin layer chromatography using a thin layer of silica gel and 2.0 g of the main component having a high purity was obtained. The main component was confirmed to be Compound B-18 from FD-MS (808).

SYNTHESIS EXAMPLE 6 (COMPOUND B-17)

The reaction was conducted in accordance with the same procedures as those conducted in Synthesis Example 1 (B) except that 2.33 g (11.7 mmole) of phenothiazine was used in place of diphenylamine. After the reaction was completed, the reaction mixture was filtered. The filtrate was washed with water, concentrated and dried and 4.2 g of a orange powdery solid was obtained. The obtained solid was dissolved in toluene and fractionated in accordance with the thin layer chromatography using a layer of silica gel and 2.6 g of the main component having a high purity was obtained. The main component was confirmed to be Compound B-17 from FD-MS (872).

SYNTHESIS EXAMPLE 7 (COMPOUND A-4)

Compound A-4 was synthesized via the reaction route shown in the following:

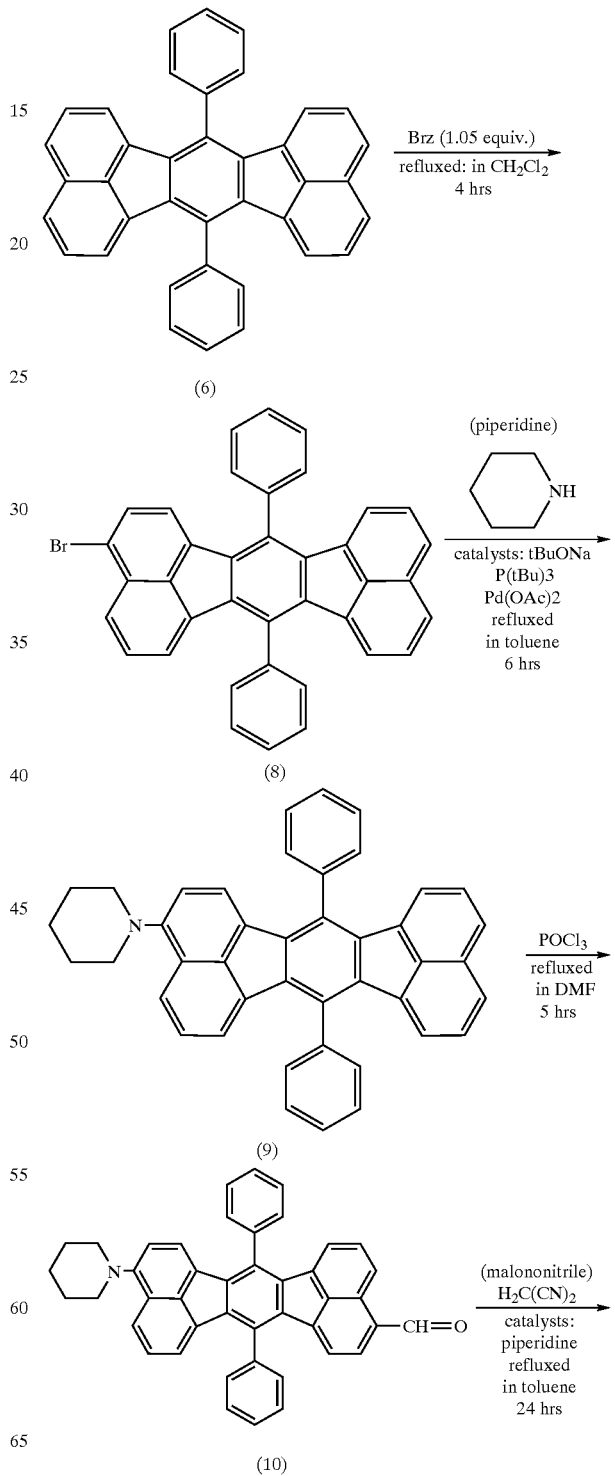

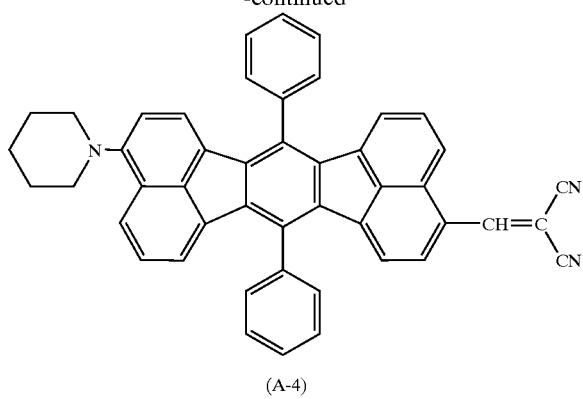

(A-4)

In the synthesis of Compound (8), the reaction mixture was examined in accordance with the thin layer chromatography and the reaction was allowed to continue until the spot of Compound (6) disappeared. After the reaction was completed, the reaction mixture was washed with a 0.1N aqueous solution of sodium hydroxide, concentrated and fractionated in accordance with the column chromatography using a column packed with silica gel and Compound (8) was obtained.

The reaction was conducted in accordance with the same procedures as those conducted in Synthesis Example 1 (B) except that 3.12 g (5.6 mmole) of Compound (8) was used in place of Compound (7) and 0.51 g (11.5 mmole) of piperidine was used in place of diphenylamine. The solid obtained by the reaction was dissolved in toluene and fractionated in accordance with the column chromatography using a column packed with silica gel and 2.2 g of Compound (9) having a high purity was obtained.

Compound (9) in an amount of 5.61 g (10.0 mmole) was dissolved into 30 ml of dimethylformamide. To the obtained solution, 1.68 g (11.0 mmole) of phosphorus oxychloride was added and the mixture was refluxed under heating. After the reaction was completed, the reaction mixture was filtered and the filtrate was fractionated in accordance with the column chromatography using a column packed with silica gel and 4.0 g of the main component having a high purity was obtained. The main component was confirmed to be Compound (10) from FD-MS (589).

Compound (10) in an amount of 4.7 g (8.0 mmole) was reacted with 0.7 g (10.6 mmole) of malonitrile. The reaction product precipitated in the reaction mixture was separated and dissolved in tetrahydrofuran. The obtained solution was fractionated in accordance with the thin layer chromatography using a thin layer of silica gel and 3.6 g of red orange crystals having a high purity were obtained. The crystals were confirmed to be Compound A-4 from FD-MS (637).

SYNTHESIS EXAMPLE 8 (COMPOUND A-14)

Compound A-14 was synthesized via the reaction route shown in the following (S. H. Tucker, J. Chem. Soc., 1462 (1958)):

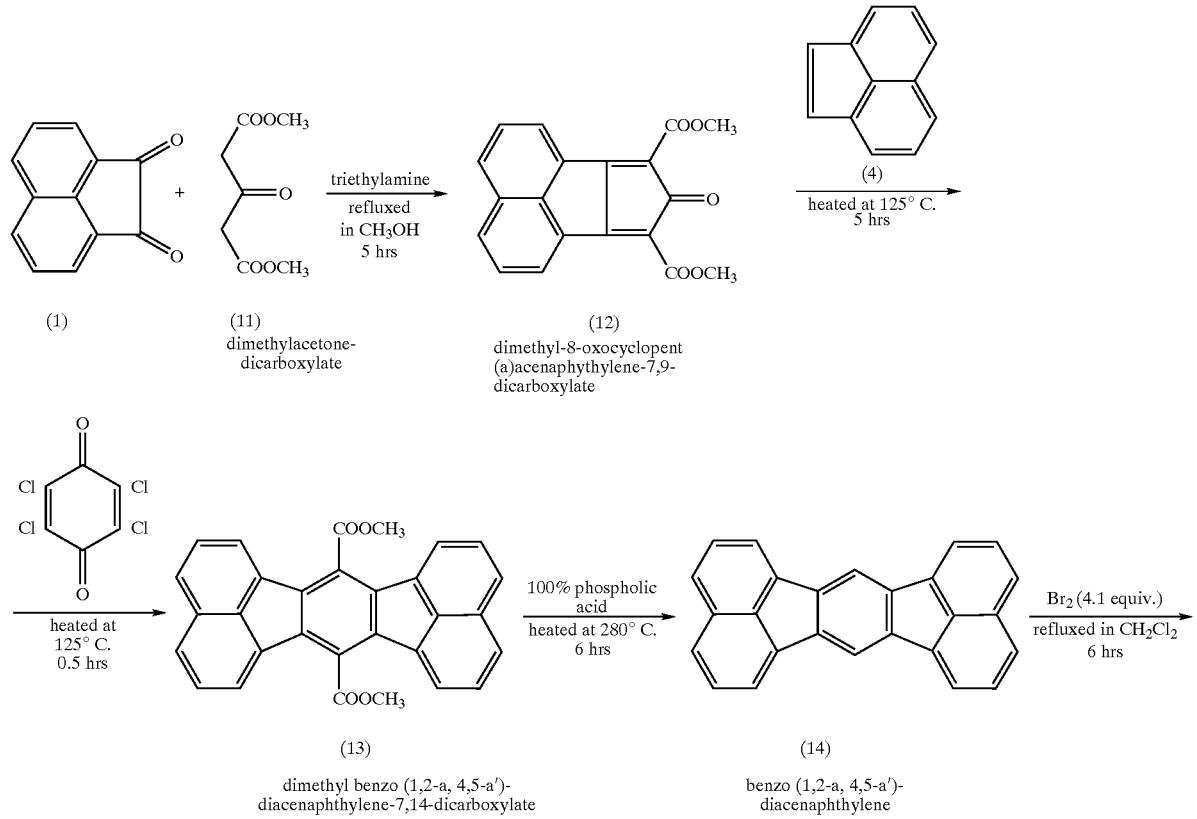

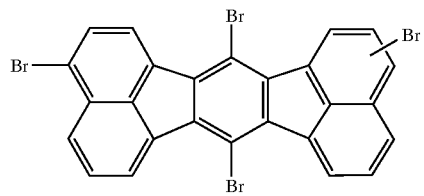
(15)
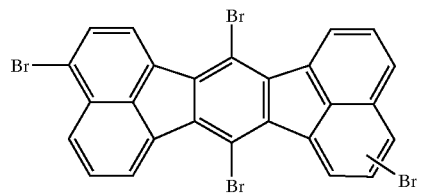
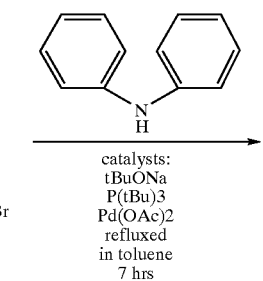
catalysts:
tBuONa
P(tBu)3
Pd(OAc)2
refluxed
in toluene
7 hrs
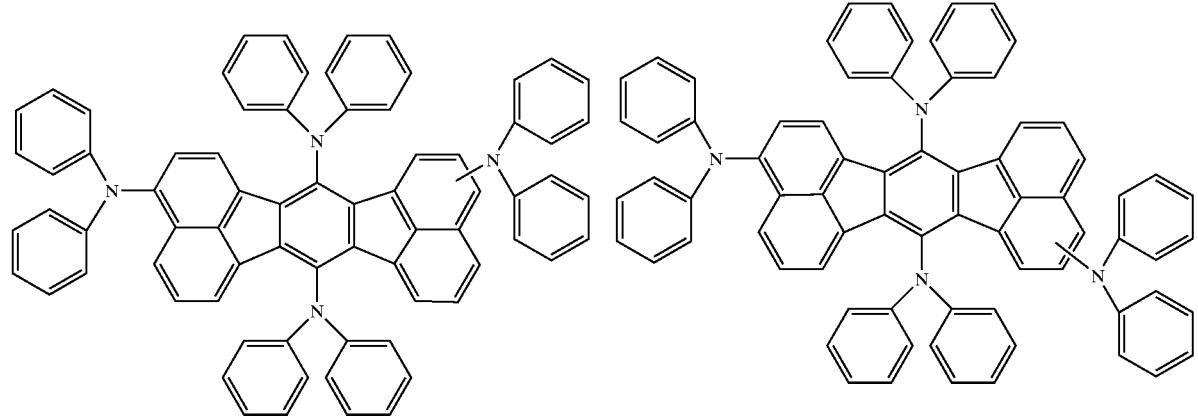
(A-14)
* (1) ⟶ (14)
cf. S.H. Tucker  J. Chem.Soc:1462 (1958)
SYNTHESIS EXAMPLE 9 (COMPOUND A-6)
Compound A-6 was synthesized via the reaction route shown in the following:
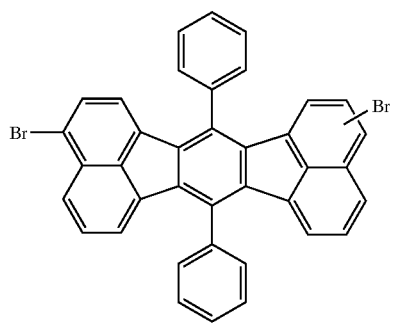
catalysts:
tBuONa
P(tBu)3
Pd(OAc)2
at 40° C.
in toluene
15hrs
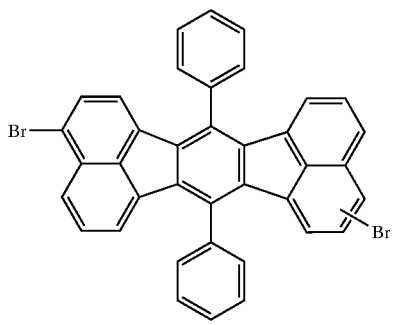
(7)
(A-6)
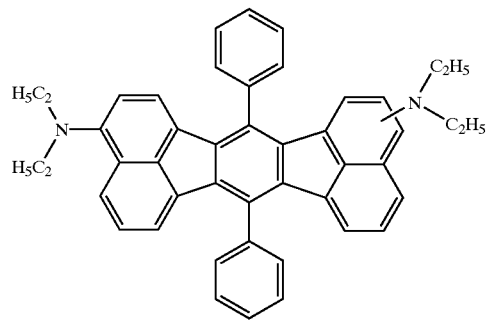
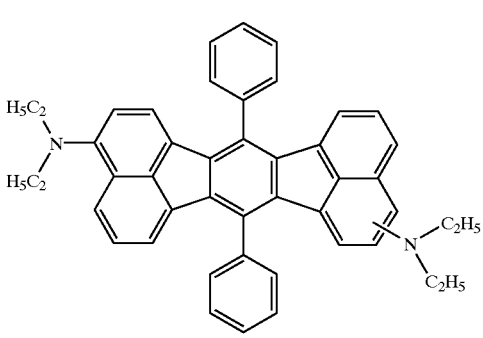
SYNTHESIS EXAMPLE 10 (COMPOUND B-5)
Compound B-5 was synthesized via the reaction route shown in the following (Beil. 5(3) 2278):

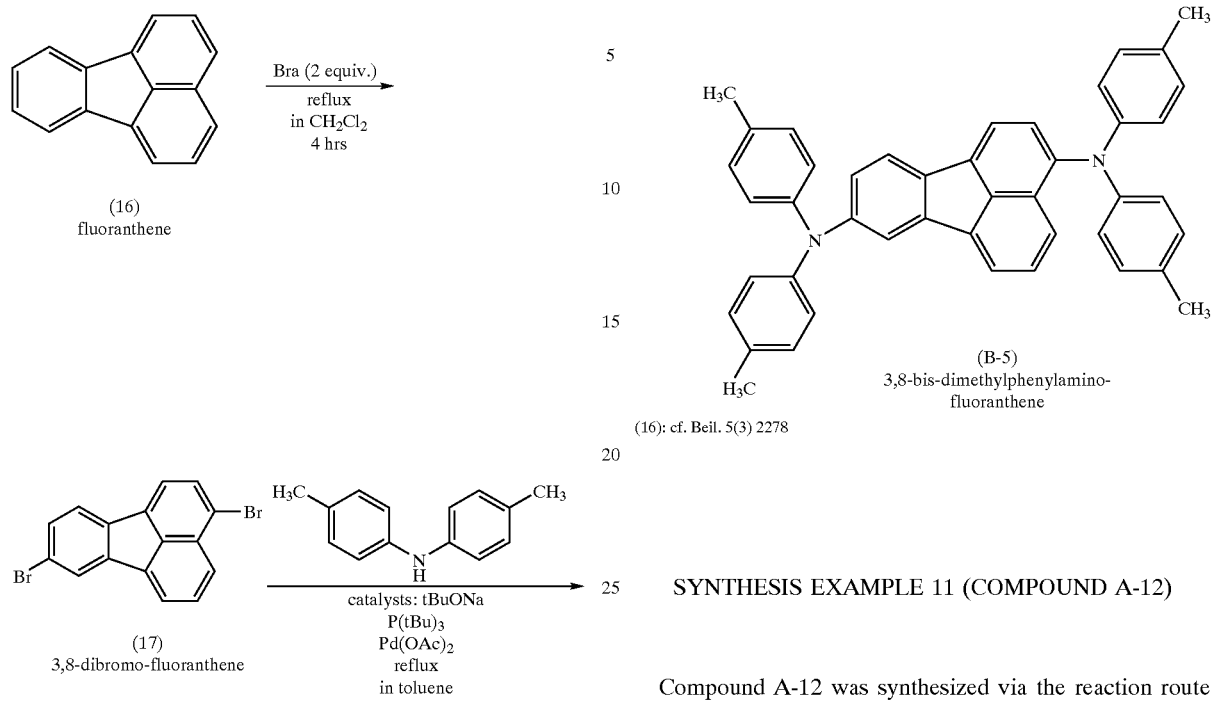
(16): cf. Beil. 5(3) 2278
SYNTHESIS EXAMPLE 11 (COMPOUND A-12)
Compound A-12 was synthesized via the reaction route shown in the following:
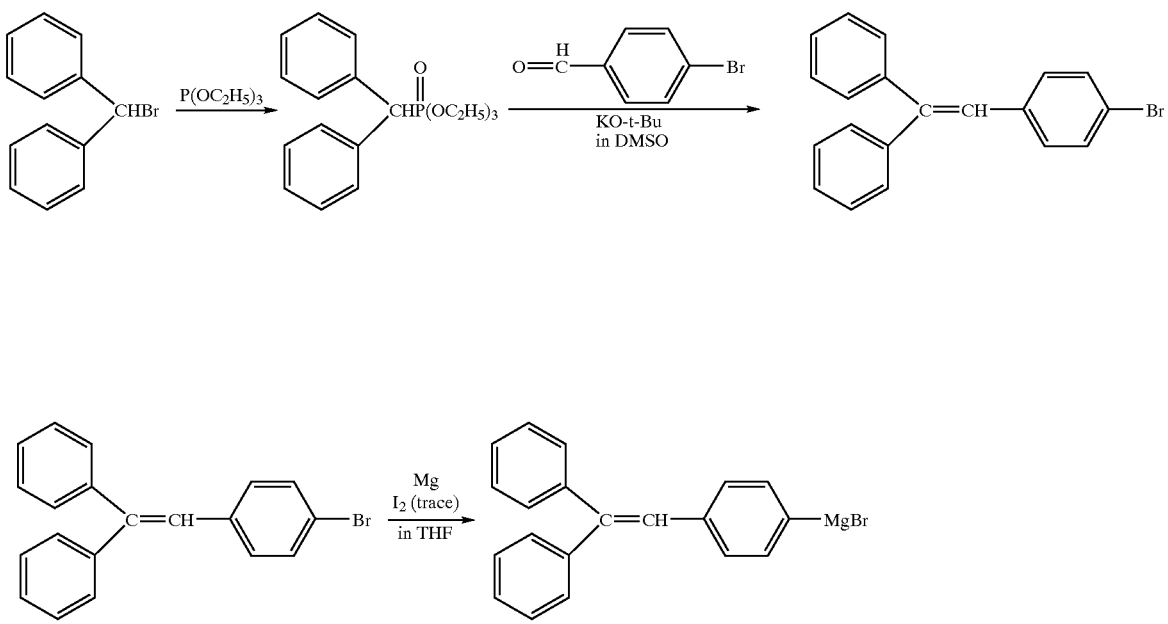

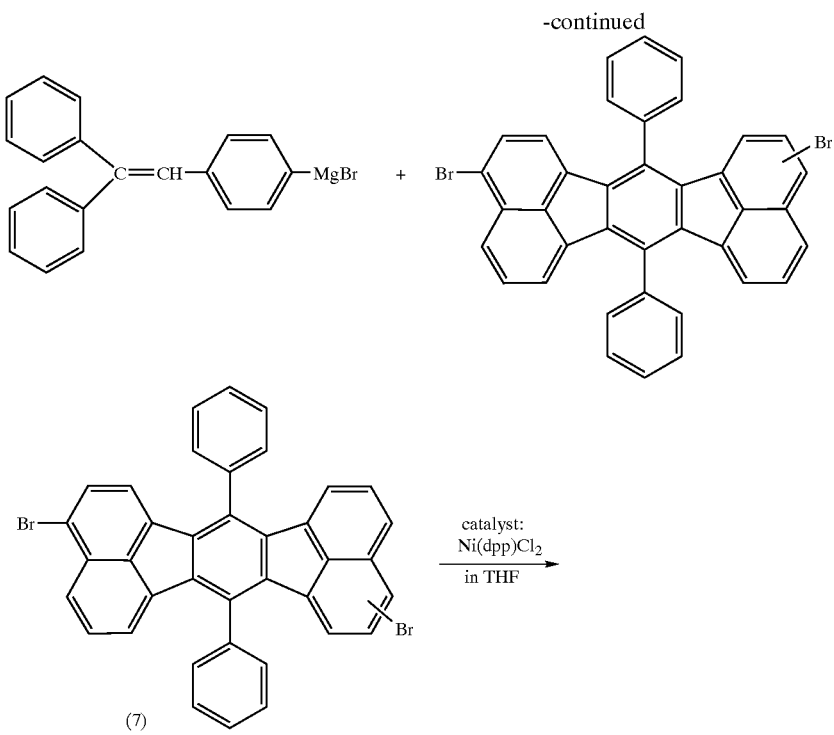
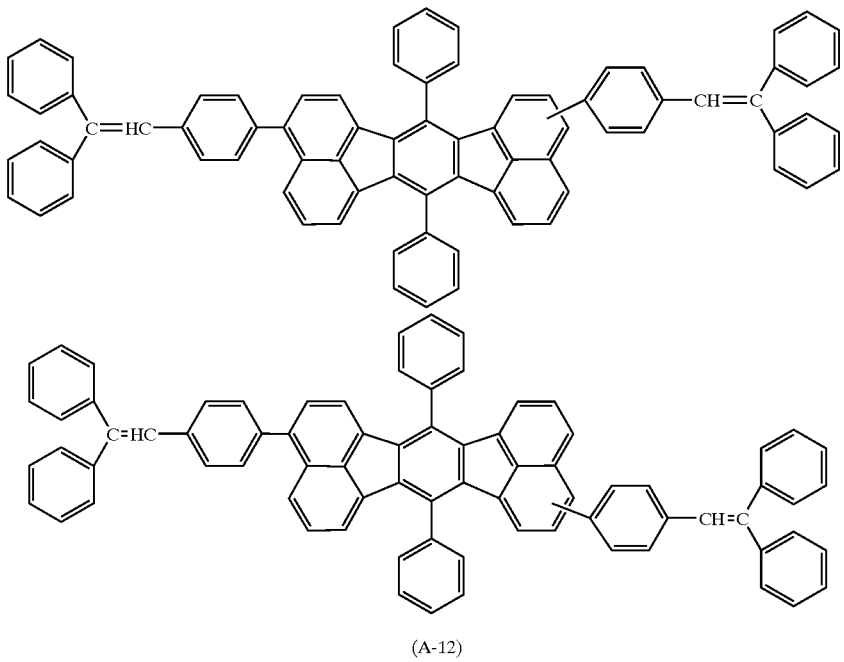
SYNTHESIS EXAMPLE 12
A composition containing 3,10-bisdiphenylamino-7,14-diphenylacenaphtho[1,2-k]fluoranthene and 3,11-bisdiphenylamino-7,14-diphenylacenaphtho[1,2-k]fluoranthene in a ratio of the amounts by mole in the range of 20:80 to 30:70 was synthesized via the reaction route shown in the following:

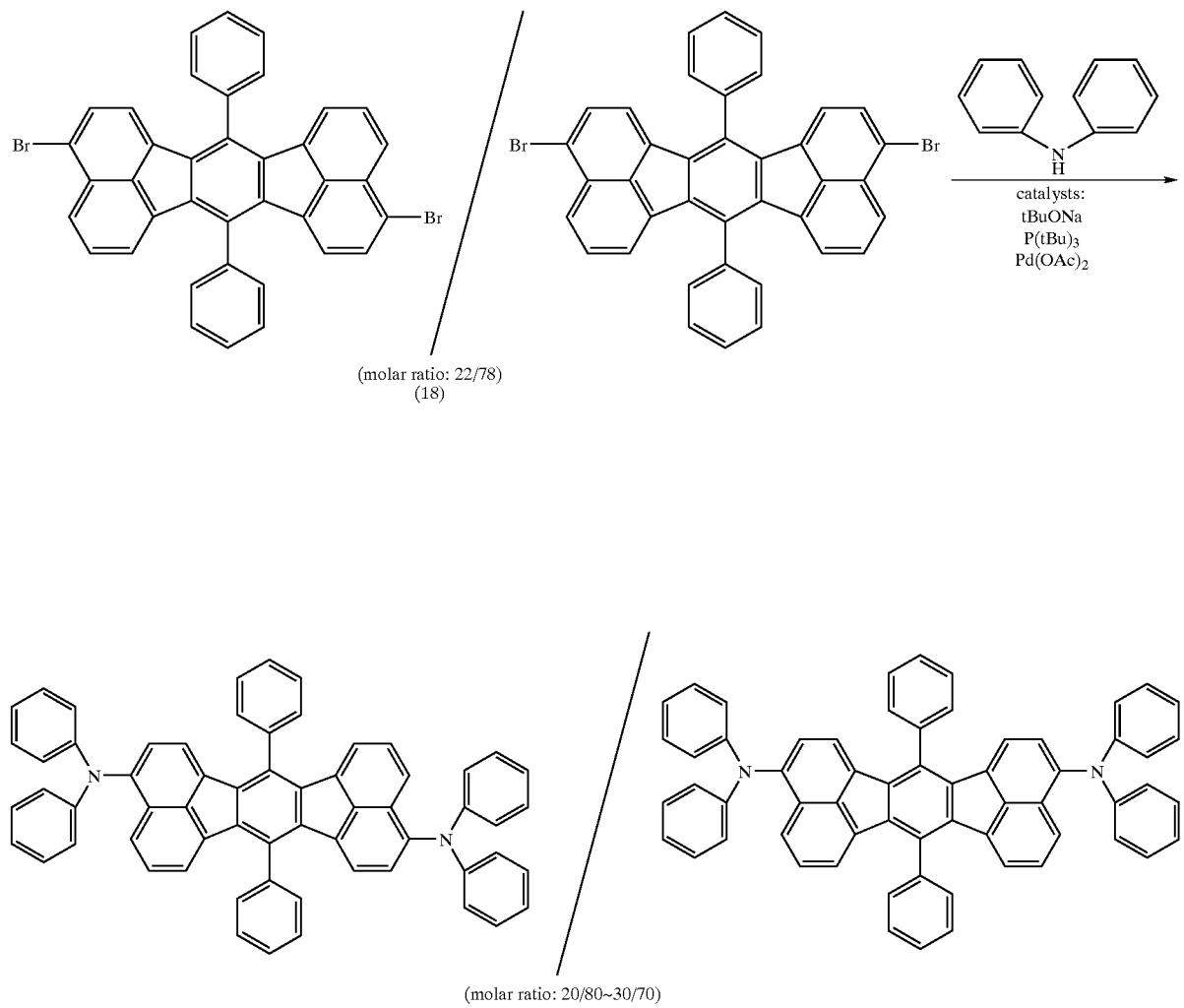

(molar ratio: 22/78)
(18)

(molar ratio: 20/80~30/70)

(A) Synthesis of a Composition (18) Containing 3,10- and 3,11-dibromo-7,14-diphenylacenaphtho[1,2-k]fluoranthenes in a Ratio of the Amounts by Mole of 22:78

The solution portion of the reaction mixture obtained in Synthesis Example 1 (A) was concentrated, dissolved in tetrahydrofuran and recrystallized and the formed precipitates were removed. The solution portion was concentrated and a dibromo compound was obtained. This dibromo compound was confirmed to be a composition containing 3,10- and 3,11-dibromo-7,14-diphenylacenaphtho[1,2-k]fluoranthenes in a ratio of the amounts by mole of 22:78 from the $^1$H-NMR spectrum.

(B) Synthesis of a Composition Containing 3,10- and 3,11-bisdiphenylamino-7,14-diphenylacenaphtho[1,2-k]fluoranthenes in a Ratio by the Amounts by Mole in the Range of 20:80 to 30:70

Into 100 ml of toluene, 5.00 g (7.9 mmole) of the composition containing 3,10- and 3,11-dibromo-7,14-diphenylacenaphtho[1,2-k]fluoranthenes in a ratio of the amounts by mole of 22:78 (18), 2.78 g (16.5 mmole) of diphenylamine, 0.09 g (0.09 mmole) of palladium acetate, 0.44 g (2.2 mmole) of tri-tert-butylphosphine and 2.12 g (19.6 mmole) of sodium tert-butoxide were dissolved and the reaction was allowed to proceed for 6 hours while the mixture was refluxed under heating. After the reaction was completed, the reaction mixture was filtered. The filtrate was concentrated and fractionated in accordance with the column chromatography using a column packed with silica gel and 6.20 g of a red orange powdery solid was obtained. This solid was confirmed to be a composition containing 3,10-bisdiphenylamino-7,14-diphenylacenaphtho[1,2-k]fluoranthene and 3,11-bisdiphenylamino-7,14-diphenylacenaphtho[1,2-k]fluoranthene in a ratio of the amounts by mole in the range of 20:80 to 30:70 from FD-MS (812) and the $^1$H-NMR spectrum (H: 400 MHz; the solvent of the measurement: DMSO (120° C.); shown in FIG. 1).

SYNTHESIS EXAMPLE 13

5,12- and/or 5,13-Bisdiphenylamino-9,16-diphenylfluorantheno[8,9-a]aceanthrylenes were synthesized via the reaction route shown in the following:

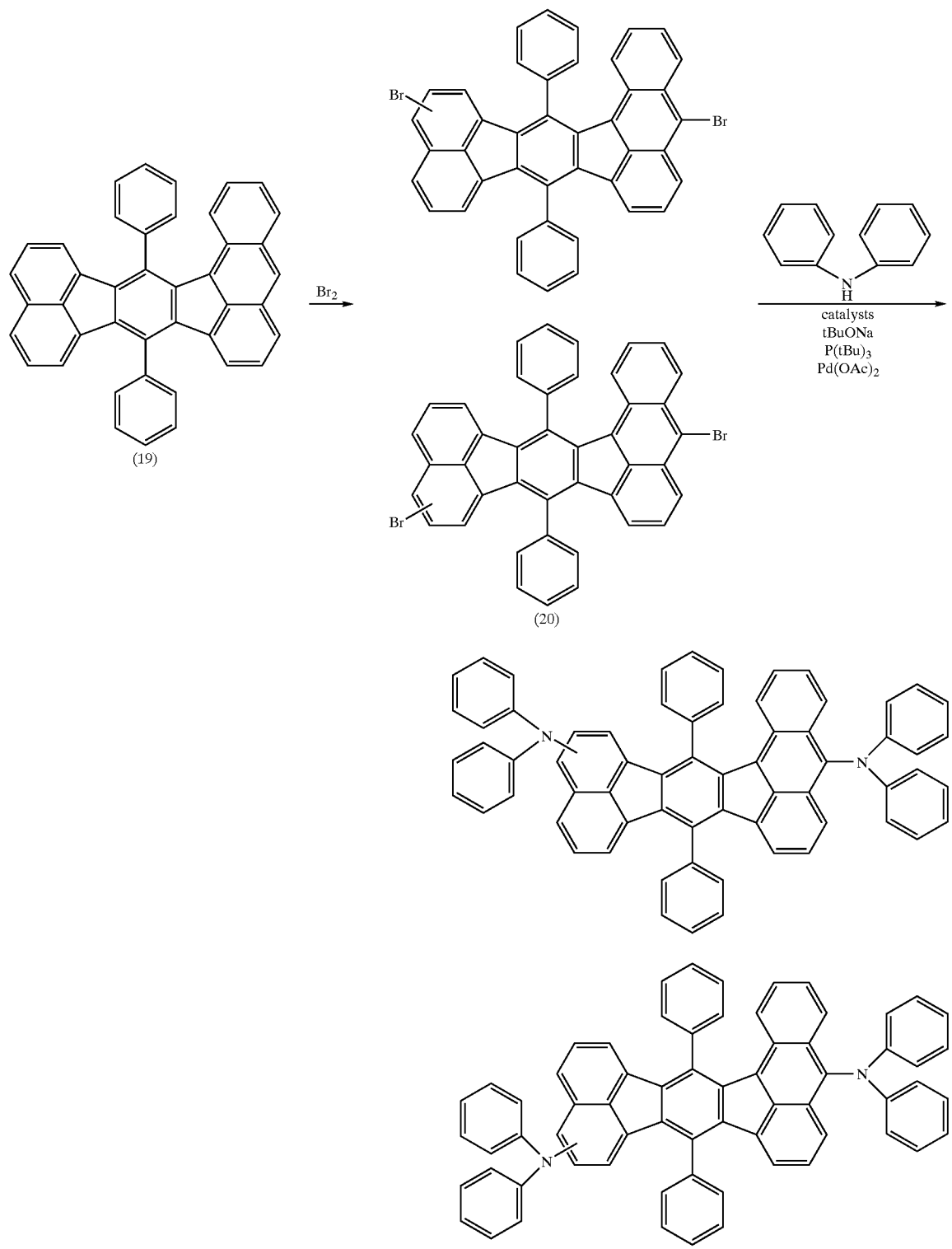

(A) Synthesis of 9,16-diphenylfluorantheno[8,9-a]aceanthrylene (19)

With reference to the Bandyopadhyai's process, 9,16-diphenylfluorantheno[8,9-a]aceanthrylene was synthesized by the reaction of 1,3-diphenylcyclopenta[a]aceanthrylen-2-one and acenaphthylene using aceanthrylenequinone as the starting material [Indian J. Chem., Vol. 21B, 91 (1982)].

(B) Synthesis of 5,12- and/or 5,13-dibromo-9,16-diphenylfluorantheno[8,9-a]aceanthrylene (20)

Into 240 ml of methylene chloride, 4.00 g (7.6 mmole) of 9,16-diphenylfluorantheno[8,9-a]aceanthrylene (19) was dissolved. While the obtained mixture was refluxed under heating, 18.0 ml of a 1M methylene chloride solution of bromine was added dropwise and the reaction was allowed to proceed for 2 hours. The resultant reaction mixture was washed with an aqueous solution of sodium hydroxide and pure water and concentrated and 5.06 g of a yellow brown powdery solid was obtained. The solid was confirmed to be 5,12-dibromo-9,16-diphenylfluorantheno[8,9-a]aceanthrylene and/or 5,13-dibromo-9,16-diphenylfluorantheno[8,9-a]aceanthrylene from FD-MS (686) and the ¹H-NMR spectrum.

Figure 2:
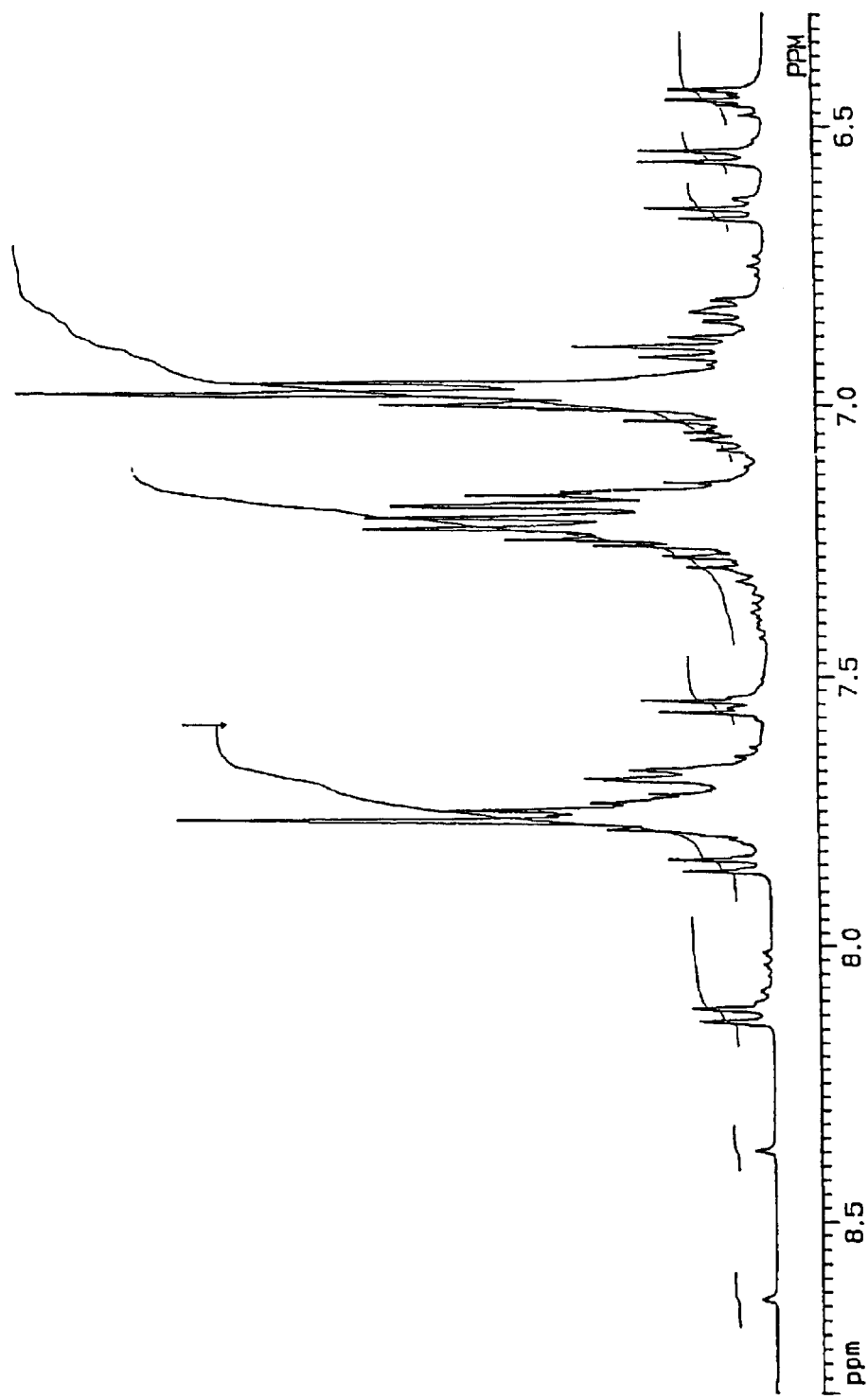
FIG. 2 shows the $^1$H-NMR spectrum of another example of the novel compound of the present invention.

(C) Synthesis of 5,12- and/or 5,13-bisdiphenylamino-9,16-diphenylfluorantheno[8,9-a]aceanthrylene Into 200 ml of toluene, 5.00 g (7.4 mmole) of 5,12- and/or 5,13-dibromo-9,16-diphenylfluorantheno[8,9-a]aceanthrylene (20), 2.75 g (16.2 mmole) of diphenylamine, 0.09 g (0.4 mmole) of palladium acetate, 0.43 g (2.2 mmole) of tri-tert-butylphosphine and 2.05 g (20.6 mmole) of sodium tert-butoxide were dissolved and the reaction was allowed to proceed for 5 hours while the mixture was refluxed under heating. After the reaction was completed, the reaction mixture was filtered. The filtrate was concentrated and fractionated in accordance with the column chromatography using a column packed with silica gel and 4.27 g of a black purple powdery solid of the main component was obtained. The main component was confirmed to be 5,12- and/or 5,13-bisdiphenylamino-9,16-diphenylfluorantheno[8,9-a]aceanthrylene from FD-MS (862) and the ¹H-NMR spectrum (H: 400 MHz; the solvent of the measurement: DMSO (120° C.); shown in FIG. 2).

SYNTHESIS EXAMPLE 14

3,11- and/or 3,12-Bisdiphenylamino-7,16-diphenylfluorantheno[8,9-k]fluoranthene was synthesized via the reaction route shown in the following:

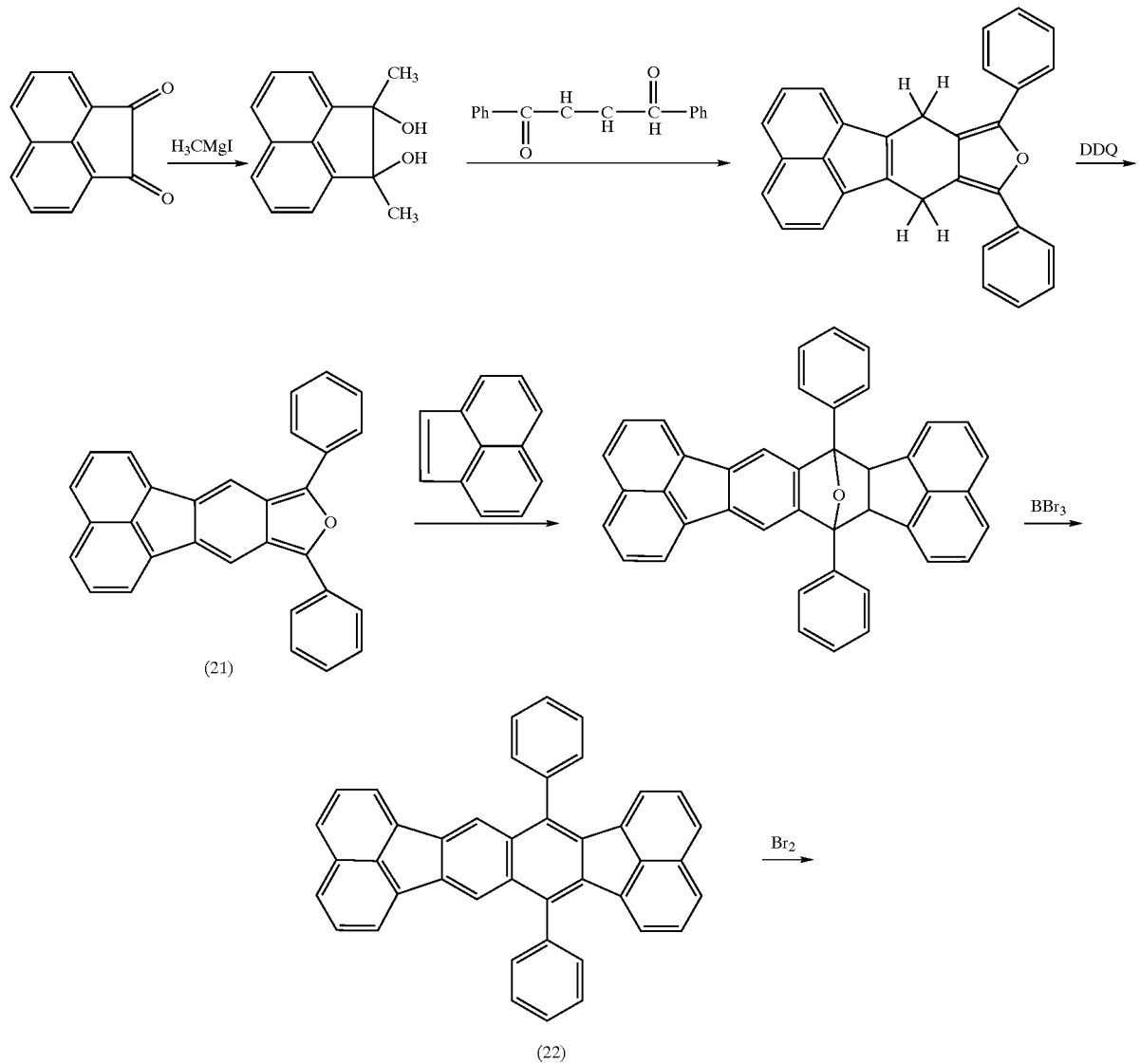

-continued
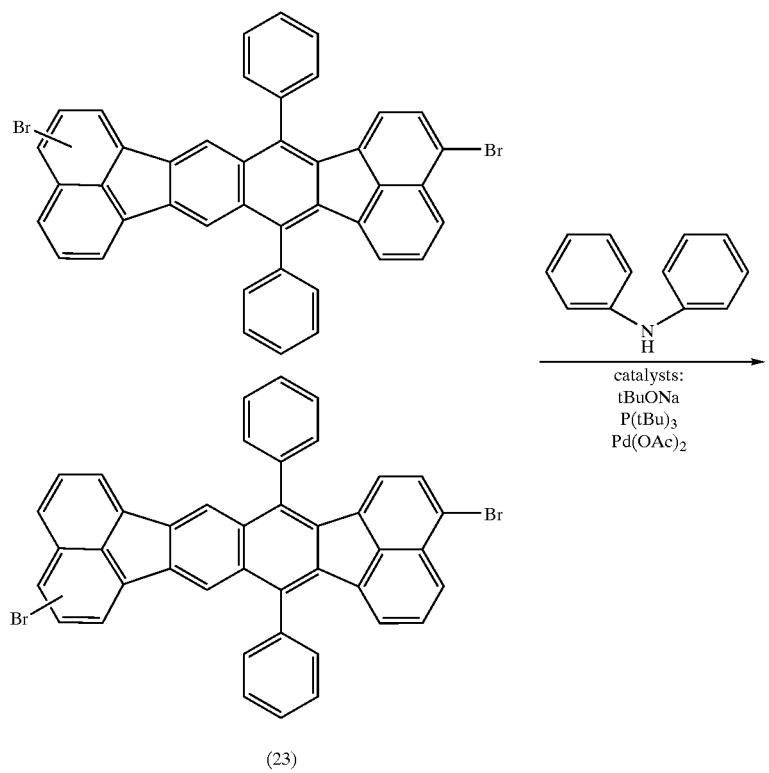
(23)
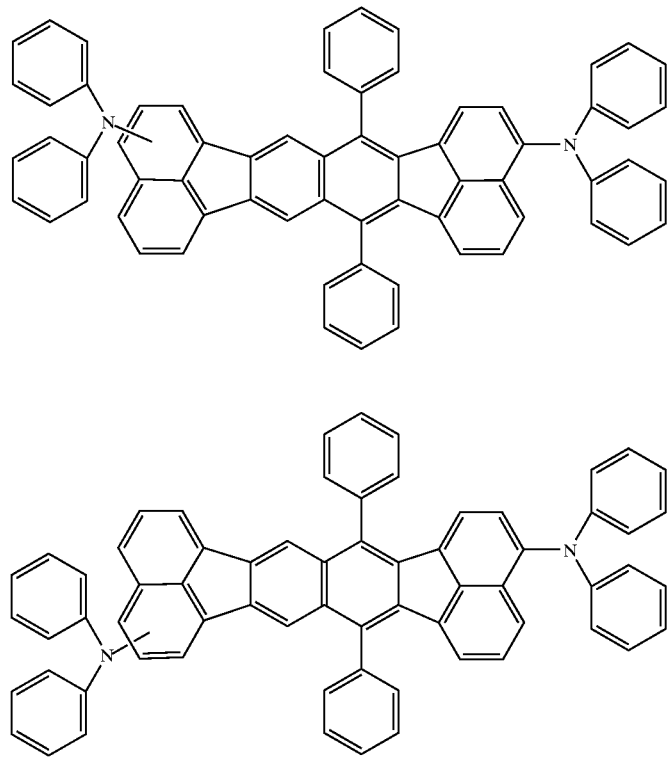

(A) Synthesis of 2,5-diphenylfluorantheno[11',12'-3,4]furan (21)

In accordance with the N. Campbell's process [J. Chem. Soc., 1555 (1949)], 2,5-diphenylfluorantheno[11',12'-3,4]furan (21) was synthesized by the reaction of 7,8-dimethylacenaphthene-7,8-diol which was synthesized in accordance with the S. H. Tucker's process [J. Chem. Soc., 1462 (1958)] and trans-1,2-dibenzoylethylene.

(B) Synthesis of 7,16-diphenylfluorantheno[8,9-k]fluoranthene (22)

Into a mixed solvent containing 500 ml of xylene and 660 ml of methylene chloride, 5.00 g (12.7 mmole) of 2,5-diphenylfluorantheno[11',12'-3,4]furan (21) and 3.86 g (19.0 mmole) of acenaphthylene were added and the mixture was refluxed under heating for 3 hours. The solution was cooled and 16.0 ml of a 1M methylene chloride solution of $BBr_3$ was added dropwise to the cooled solution. The obtained solution was heated at 60° C. for 4 hours. The resultant reaction mixture was washed with an aqueous solution of sodium hydrogencarbonate and pure water, concentrated and purified in accordance with the column chromatography using a column packed with silica gel and 3.20 g of yellow crystals were obtained. The crystals were confirmed to be 7,16-diphenylfluorantheno[8,9-k]fluoranthene (22) from FD-MS (528) and the $^1$H-NMR spectrum.

(C) Synthesis of 3,11- and/or 3,12-dibromo-7,16-diphenylfluorantheno[8,9-k]fluoranthene (23)

Into 230 ml of methylene chloride, 2.30 g (4.3 mmole) of 7,16-diphenylfluorantheno[8,9-k]fluoranthene (22) was dissolved. While the obtained solution was refluxed under heating, 9.0 ml of a 1M methylene chloride solution of bromine was added dropwise to the solution and then the reaction was allowed to proceed for 2 hours. The resultant reaction mixture was washed with an aqueous solution of sodium hydroxide and pure water and concentrated and 3.06 g of a light yellow brown crystals were obtained. The crystals were confirmed to be 3,11- and/or 3,12-dibromo-7,16-diphenylfluorantheno[8,9-k]fluoranthene (23) from FD-MS (686) and the $^1$H-NMR spectrum.

Figure 3:
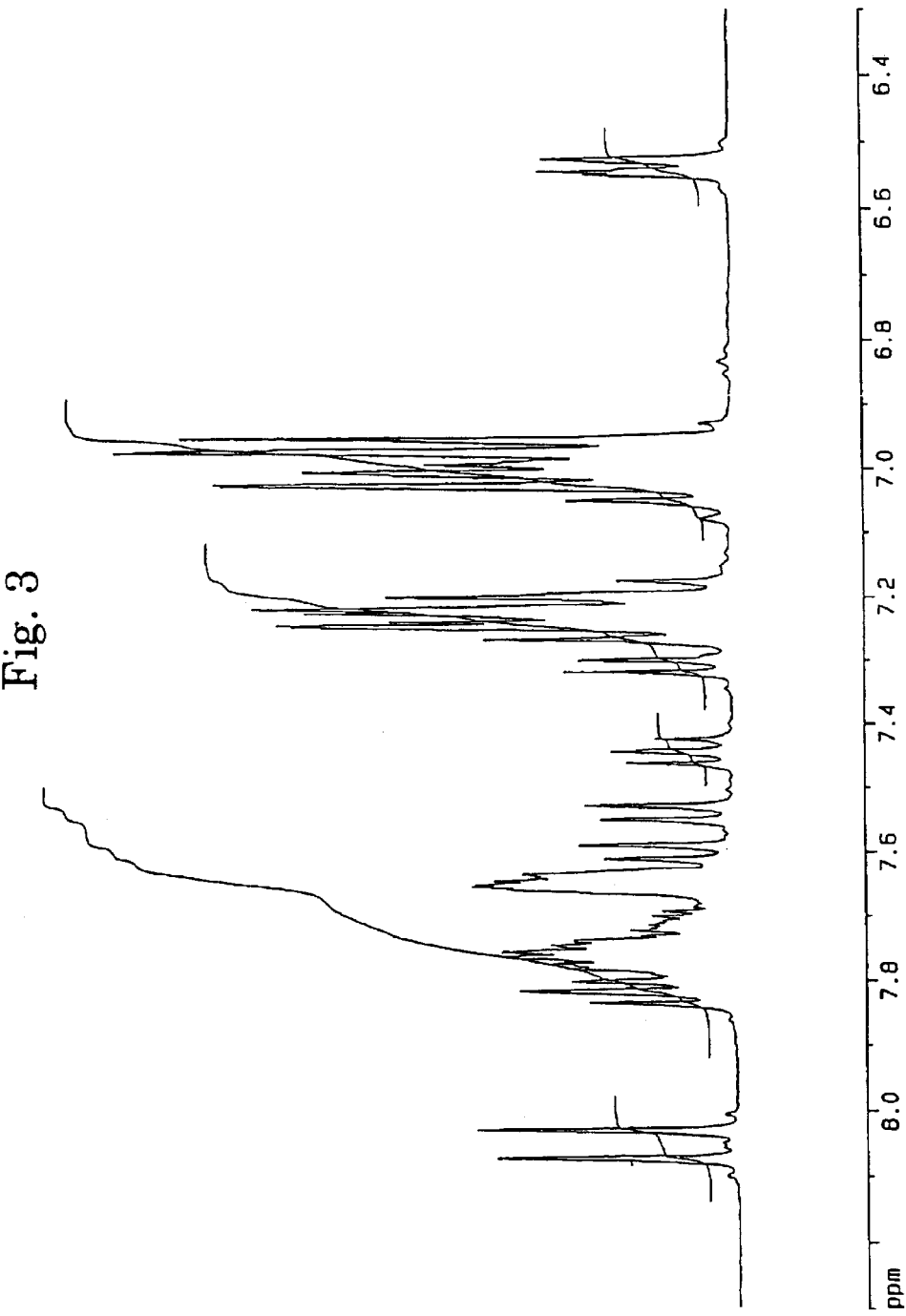
FIG. 3 shows the $^1$H-NMR spectrum of still another example of the novel compound of the present invention.

(D) Synthesis of 3,11- and/or 3,12-bisdiphenylamino-7,16-diphenylfluorantheno[8,9-k]fluoranthene Into 120 ml of toluene, 3.92 g (5.7 mmole) of 3,11- and/or 3,12-dibromo-7,16-diphenylfluorantheno[8,9-k]fluoranthene (23), 2.03 g (12.0 mmole) of diphenylamine, 0.07 g (0.07 mmole) of palladium acetate, 0.33 g (1.7 mmole) of tri-tert-butylphosphine and 1.56 g (14.4 mmole) of sodium tert-butoxide were dissolved and the reaction was allowed to proceed for 6 hours while the mixture was refluxed under heating. After the reaction was completed, the reaction mixture was filtered. The filtrate was purified in accordance with the column chromatography using a column packed with silica gel and 4.27 g of a orange powdery crystals were obtained. The crystals were confirmed to be 3,11- and/or 3,12-bisdiphenylamino-7,16-diphenylfluorantheno[8,9-k]fluoranthene from FD-MS (862) and the $^1$H-NMR spectrum (H: 400 MHz; the solvent of the measurement: DMSO (120° C.); shown in FIG. 3).

SYNTHESIS EXAMPLE 15

A composition containing 3,10-bisditolylamino-7,14-diphenylacenaphtho[1,2-k]fluoranthene and 3,11-bisditolylamino-7,14-diphenylacenaphtho[1,2-k]fluoranthene in a ratio of the amounts by mole in the range of 80:20 to 90:10 was synthesized.

(A) Synthesis of a Composition (18) Containing 3,10- and 3,11-dibromo-7,14-diphenylacenaphtho[1,2-k]fluoranthenes The solution portion of the reaction mixture obtained in Synthesis Example 1 (A) was concentrated, dissolved entirely in tetrahydrofuran and recrystallized and the formed precipitates were removed. The solution portion was concentrated and a dibromo compound was obtained. This dibromo compound was confirmed to be a composition containing 3,10- and 3,11-dibromo-7,14-diphenylacenaphtho[1,2-k]fluoranthenes containing in a ratio of the amounts by mole in the range of 80:20 to 90:10 from the $^1$H-NMR spectrum.

(B) Synthesis of a Composition Containing 3,10- and 3,11-bisditolylamino-7,14-diphenylacenaphtho[1,2-k]fluoranthenes in a Ratio of the Amounts by Mole in the Range of 80:20 to 90:10

In accordance with the same procedures as those conducted in Synthesis Example 12 (B) except that di-p,p-tolylamine was used in place of diphenylamine, a composition (A-16) containing 3,10- and 3,11-bisditolylamino-7,14-diphenylacenaphtho[1,2-k]fluoranthenes in a ratio of the amounts by mole in the range of 80:20 to 90:10 was synthesized.

SYNTHESIS EXAMPLE 16

A composition containing 3,10-bisdiphenylamino-7,14-diphenylacenaphtho[1,2-k]fluoranthene and 3,11-bisdiphenylamino-7,14-diphenylacenaphtho[1,2-k]fluoranthene in a ratio of the amounts by mole in the range of 80:20 to 90:10 was synthesized.

(A) Synthesis of a Composition (18) Containing 3,10- and 3,11-dibromo-7,14-diphenylacenaphtho[1,2-k]fluoranthenes The composition containing the dibromo compounds was obtained in accordance with the same procedures as those conducted in Synthesis Example 15 (A).

(B) Synthesis of a Composition (A-1) Containing 3,10- and 3,11-bisdiphenylamino-7,14-diphenyloacenaphtho[1,2-k]fluoranthenes in a Ratio of the Amounts by Mole in the Range of 80:20 to 90:10

In accordance with the same procedures as those conducted in Synthesis Example 12 (B) using the composition obtained above in (A), a composition containing 3,10-bisdiphenylamino-7,14-diphenylacenaphtho[1,2-k]fluoranthene and 3,11-bisdiphenylamino-7,14-diphenylacenaphtho[1,2-k]fluoranthene in a ratio of the amounts in mole in the range of 80:20 to 90:10 was synthesized.

EXAMPLE 1

On a cleaned glass plate having an ITO electrode, the following compound (H232) as the hole injecting material was vapor deposited so that a film having a thickness of 60 nm was formed.

(H232)

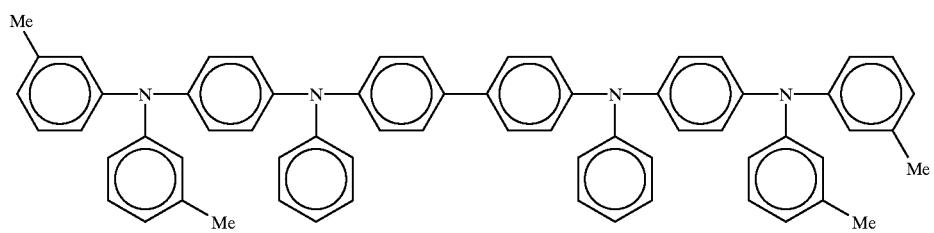

Then, the following compound (NPD) as the hole transporting material was vapor deposited so that a film having a thickness of 20 nm was formed.

(NPD)

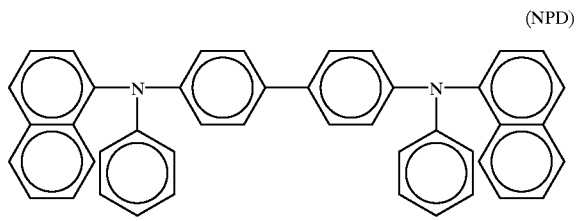

Subsequently, an aluminum complex of 8-hydroxyquinoline (Alq) and 3,10- and 3,11-diphenylamino-7,14-diphenylacenaphthofluoranthenes (Compound A-1) as the materials for the light emitting layer were vapor deposited so that a film containing 2.1% by mole of Compound A-1 and having a thickness of 50 nm was formed. The structure of Alq is shown in the following:

(Alq)

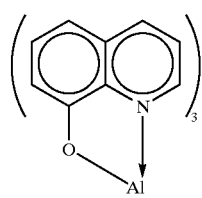

An electron injecting layer was formed by vapor deposition of Alq alone so that the formed film had a thickness of 10 nm. A layer of an inorganic compound was formed on the electron injecting layer by vapor deposition of LiF so that the formed film had a thickness of 0.2 nm. On the thus formed layer, aluminum was vapor deposited so that an electrode having a thickness of 170 nm was formed and an organic EL device was obtained. The vapor depositions for forming the above layers were conducted under $10^{-6}$ Torr while the substrate was kept at the room temperature.

The light emitting property of this device was as follows: the luminance under application of a direct current of 5.5 V: 103 cd/m$^2$; the efficiency of light emission: as high as 6.2 cd/A. The emitted light was orange light having chromaticity coordinates of (0.56, 0.44). When the device was driven under a constant current at an initial luminance of 500 cd/m$^2$, the half-life was as long as 2600 hours.

This example shows that an organic EL device exhibiting a high performance can be obtained by using Compound A-1 as the doping material. The spectrum of the light emitted by the device was obtained and found to be the same as the fluorescence spectrum of the doping material. Thus, it is shown that the doping material worked as the center of light emission.

COMPARATIVE EXAMPLE 1

An organic EL device was obtained in accordance with the same procedures as those conducted in Example 1 except that rubrene was vapor deposited in place of Compound A-1 so that a film containing 4.0% by mole of rubrene was formed.

The light emitting property of this device was as follows: the luminance under application of a direct current of 5.5 V: 105 cd/m$^2$; the efficiency of light emission: 7.6 cd/A. However, the emitted light was yellow light having chromaticity coordinates of (0.50, 0.50). The half-life was 1000 hours when the device was driven under a constant current at an initial luminance of 500 cd/m$^2$ and shorter than that of the device of Example 1.

COMPARATIVE EXAMPLE 2

An organic EL device was obtained in accordance with the same procedures as those conducted in Example 1 except that fluorantheno[8,9-k]fluoranthene described in Japanese Patent Application Laid-Open No. Heisei 11(1999)-40360 was vapor deposited in place of Compound A-1 so that a film containing 2% by mole of this fluoranthene was formed.

The light emitting property of this device was as follows: the luminance under application of a direct current of 5.5 V: 35 cd/m$^2$; the efficiency of light emission: 3.0 cd/A. The emitted light was yellow green light. The half-life was as short as 300 hours when the device was driven under a constant current at an initial luminance of 500 cd/m$^2$.

COMPARATIVE EXAMPLE 3

An organic EL device was obtained in accordance with the same procedures as those conducted in Example 1 except that 7,14-diphenylacenaphtho[1,2-k]fluoranthene described in Japanese Patent Application Laid-Open No. Heisei 11(1999)-168445 was vapor deposited in place of Compound A-1 so that a film containing 2% by mole of this fluoranthene was formed.

The light emitting property of this device was as follows: the luminance under application of a direct current of 6 V: 69 cd/m$^2$; the efficiency of light emission: 1.3 cd/A. The emitted light was yellow green light. The efficiency was smaller than that of a device in which Alq alone was used as the light emitting material. The half-life was as short as 400 hours when the device was driven under a constant current at an initial luminance of 500 cd/m$^2$. When the spectrum of the light emitted by the device was obtained, the spectrum did not agree with the fluorescence spectrum of the doping material. Thus, it was found that the above compound did not emit light and the yellow green light was emitted from Alq. The doping material did not work as the light emitting material.

EXAMPLE 2 TO 11

Organic EL devices were obtained in accordance with the same procedures as those conducted in Example 1 except that compounds shown in Table 1 were vapor deposited in place of Compound A-1.

The light emitting properties of these devices were obtained in accordance with the same methods as those used in Example 1. The voltage applied in the measurements, the luminance, the efficiency of light emission, the color of the emitted light and the half-life when the device was driven under a constant current at an initial luminance of 500 cd/m$^2$ are shown in Table 1.

EXAMPLE 12

An organic EL device was obtained in accordance with the same procedures as those conducted in Example 1 except that the composition containing the prescribed relative amounts of the isomers which was obtained in Synthesis Example 12 (Compound A-1) was used for the light emitting layer in a concentration of 100% and Alq was not used.

The light emitting property of this device was as follows: the luminance under application of a direct current of 4.5 V: 80 cd/m$^2$; the efficiency of light emission: 3.5 cd/A. The half-life was as long as 2100 hours when the device was driven under a constant current at an initial luminance of 500 cd/m$^2$. The device had a longer life than that of the device of Example 1 and can be used also as the main light emitting material.

EXAMPLE 13

An organic EL device was obtained in accordance with the same procedures as those conducted in Example 1 except that the composition containing the prescribed relative amounts of the isomers which was obtained in Synthesis Example 15 (Compound A-16) was used for the light emitting layer in place of Compound A-1.

The light emitting property of this device was as follows: the luminance under application of a direct current of 5.5 V: 94 cd/m$^2$; the efficiency of light emission: 5.94 cd/A. The emitted light was reddish orange light having chromaticity coordinates of (0.60, 0.39). The half-life was as long as 3200 hours when the device was driven under a constant current at an initial luminance of 500 cd/m$^2$.

EXAMPLE 14

An organic EL device was obtained in accordance with the same procedures as those conducted in Example 1 except that the composition containing the prescribed relative amounts of the isomers which was obtained in Synthesis Example 16 (Compound A-1) was used for the light emitting layer in place of Compound A-1.

The light emitting property of this device was as follows: the luminance under application of a direct current of 6 V: 100 cd/m$^2$; the efficiency of light emission: 4.75 cd/A. The emitted light had chromaticity coordinates of (0.58, 0.42). The half-life was as long as 1800 hours when the device was driven under a constant current at an initial luminance of 500 cd/m$^2$. The light having more reddish color than that of the light emitted in Example 1 could be emitted by using the above compound. This result was obtained because the composition contained a greater amount of the isomer 3,11-bisdiphenylamino-7,14-diphenylacenaphtho[12-k]fluoranthene which could emit light having a longer wavelength.

TABLE 1

| | Compound | Voltage (V) | Luminance (cd/m$^2$) | Efficiency of light emission (cd/A) | Color of emitted light | Half-life (hour) |
|---|---|---|---|---|---|---|
| Example 2 | A-2 | 5.5 | 140 | 5.7 | reddish orange | 2800 |
| Example 3 | A-8 | 5.8 | 120 | 3.6 | orange | 2100 |
| Example 4 | A-14 | 5.2 | 120 | 6.1 | red | 2700 |
| Example 5 | A-16 | 6.0 | 170 | 4.7 | reddish orange | 3100 |
| Example 6 | B-3 | 6.0 | 160 | 3.2 | reddish orange | 1900 |
| Example 7 | B-15 | 5.5 | 130 | 2.8 | orange | 1800 |
| Example 8 | B-17 | 5.8 | 110 | 2.0 | reddish orange | 1700 |
| Example 9 | B-18 | 6.1 | 120 | 2.8 | reddish orange | 2000 |
| Example 10 | A-4 | 7.2 | 110 | 3.7 | red | 1000 |
| Example 11 | B-5 | 6.0 | 120 | 6.7 | yellowish green | 1800 |

Industrial Applicability

As described above in detail, the organic electroluminescence device of the present invention which utilizes the compound selected from the compounds represented by general formulae [1] to [18] emits yellowish to reddish light, exhibits an excellent purity of color and a high efficiency of light emission and has a long life.

Therefore, the organic electroluminescence device of the present invention is advantageously used as a light source such as a planar light emitting member of televisions and a back light of displays.

What is claimed is:

1. An organic electroluminescence device which comprises an organic layer disposed between at least one pair of electrodes, wherein the organic layer comprises a metal complex of quinoline and a compound selected from compounds represented by the following general formulae [1] to [14] and [16] to [18]:

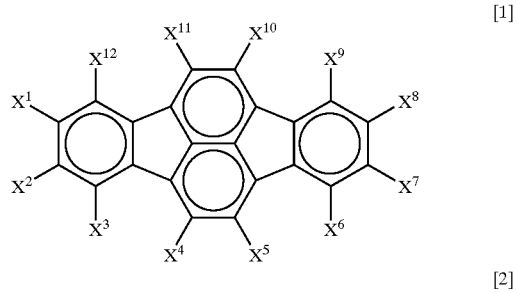

[1]

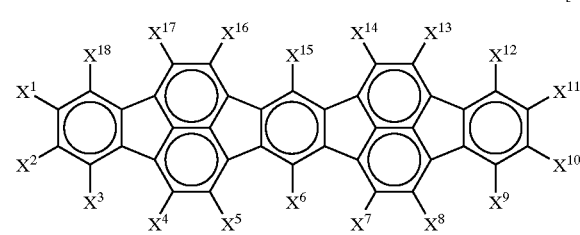

[2]

[3] 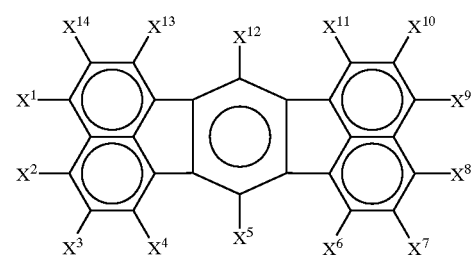
[4] 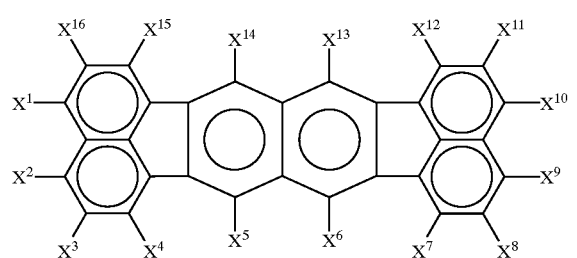
[5] 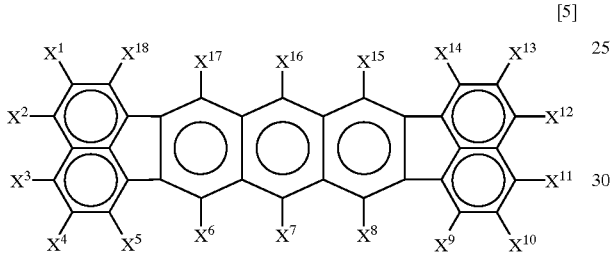
[6] 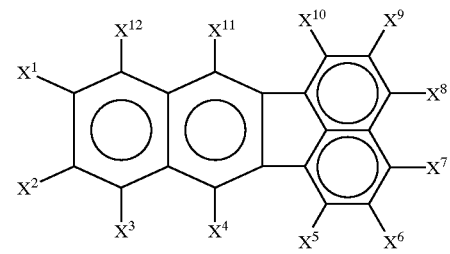
[7] 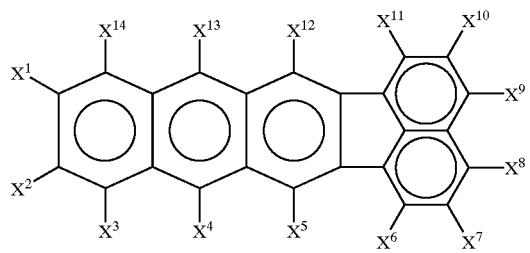
[8] 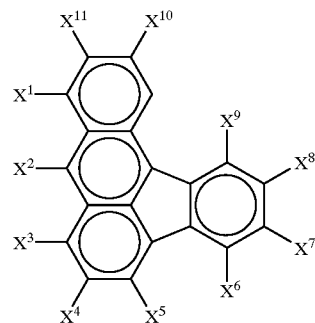
[9] 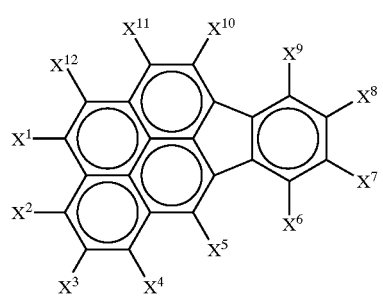
[10] 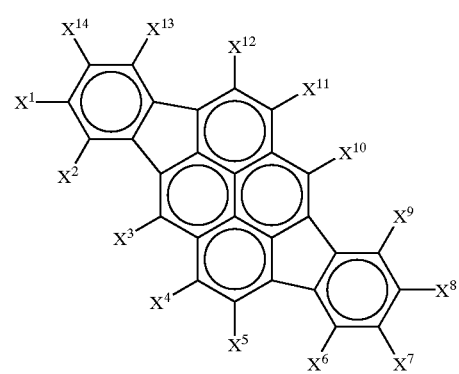
[11] 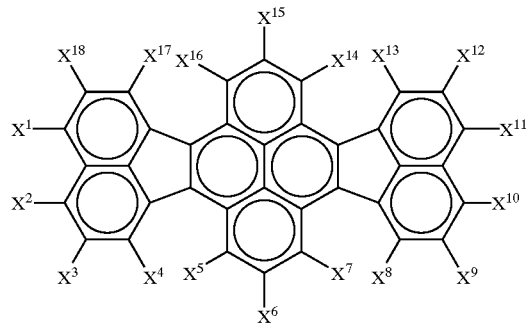
[12]
[13] 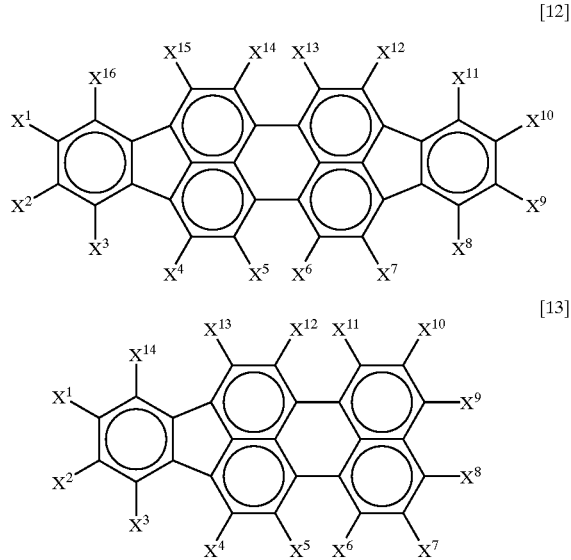

-continued

[14]

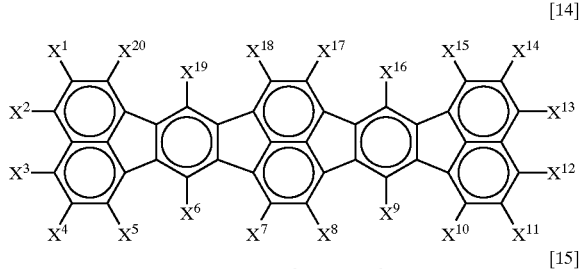

[15]

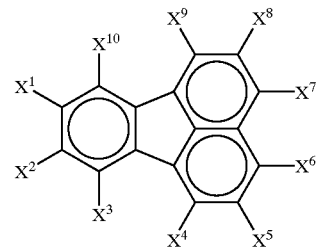

[16]

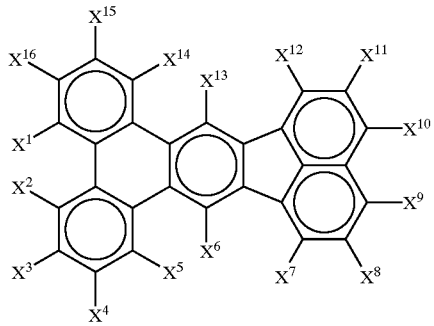

wherein $X^1$ to $X^{20}$ each independently represents hydrogen atom, a linear, branched or cyclic alkyl group having 1 to 20 carbon atoms, a linear, branched or cyclic alkoxy group having 1 to 20 carbon atoms, a substituted or unsubstituted aryl group having 6 to 30 carbon atoms, a substituted or unsubstituted aryloxy group having 6 to 30 carbon groups, a substituted or unsubstituted arylamino group having 6 to 30 carbon atoms, a substituted or unsubstituted alkylamino group having 1 to 30 carbon atoms, a substituted or unsubstituted arylalkylamino group having 7 to 30 carbon atoms or a substituted or unsubstituted alkenyl groups having 8 to 30 carbon atoms; a pair of adjacent groups represented by $X^1$ to $X^{20}$ and a pair of adjacent substituents to groups represented by $X^1$ to $X^{20}$ may form a cyclic structure in combination; when a pair of adjacent substituents are aryl groups, the pair of substituents may be a single group; and at least one of substituents represented by $X^1$ to $X^i$, i representing a number of 12 to 20, comprises an amine group or an alkenyl group;

[17]

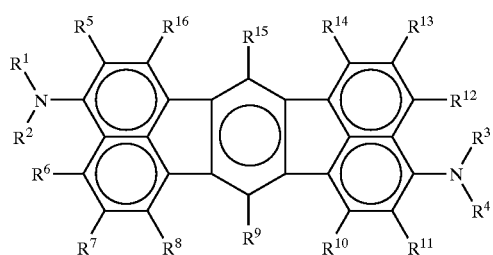

-continued

[18]

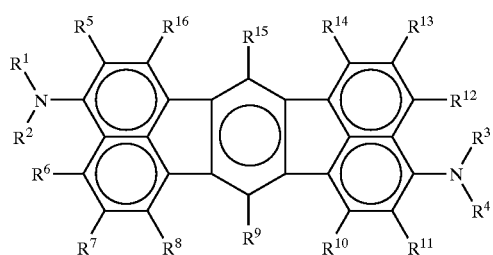

wherein $R^1$ to $R^4$ each independently represent an alkyl group having 1 to 20 carbon atoms or a substituted or unsubstituted aryl group having 6 to 30 carbon atoms; in one or both of a pair of groups represented by $R^1$ and $R^2$ and a pair of groups represented by $R^3$ and $R^4$, the groups forming the pair may be bonded through —O— or —S—; $R^5$ to $R^{16}$ represents hydrogen atom, a linear, branched or cyclic alkyl group having 1 to 20 carbon atoms, a linear, branched or cyclic alkoxy group having 1 to 20 carbon atoms, a substituted or unsubstituted aryl group having 6 to 30 carbon atoms, a substituted or unsubstituted aryloxy group having 6 to 30 carbon groups, a substituted or unsubstituted arylamino group having 6 to 30 carbon atoms, a substituted or unsubstituted alkylamino group having 1 to 30 carbon atoms, a substituted or unsubstituted arylalkylamino group having 7 to 30 carbon atoms or a substituted or unsubstituted alkenyl groups having 8 to 30 carbon atoms; a pair of adjacent groups represented by $R^5$ to $R^{16}$ and a pair of adjacent substituents to groups represented by $R^5$ to $R^{16}$ may form a cyclic structure in combination; and at least one of substituents represented by $R^5$ to $R^{16}$ comprises an amine group or an alkenyl group.

2. The organic electroluminescence device according to claim 1, wherein the metal complex of quinoline is an aluminum complex of 8-hydroxyquinoline.

3. The organic electroluminescence device according to claim 1, wherein the organic layer comprises 1 to 70% by weight of the compound which is selected from compounds represented by general formulae [1] to [14] and [16] to [18].

4. The organic electroluminescence device according to claim 1, wherein a layer of an inorganic compound is disposed between the organic layer and the electrode.

5. The organic electroluminescence device according to claim 1 which emits reddish light.

6. The organic electroluminescence device according to claim 1, wherein the organic layer comprises the compound and isomers thereof.

7. The organic electroluminescence device according to claim 6, wherein, among the compound and the isomers thereof, a ratio of an amount by mole of an isomer which can emit light having a longer wavelength to an amount by mole of an isomer which can emit light having a shorter wavelength is in a range of 90:10 to 60:40.

8. The organic electroluminescence device according to claim 6, wherein, a ratio of an amount by mole of an isomer represented by general formula [17] to an amount by mole of an isomer represented by general formula [18] is in a range of 90:10 to 60:40.

* * * * *

UNITED STATES PATENT AND TRADEMARK OFFICE
CERTIFICATE OF CORRECTION

PATENT NO. : 6,818,327 B2
DATED : November 16, 2004
INVENTOR(S) : Tagami et al.

It is certified that error appears in the above-identified patent and that said Letters Patent is hereby corrected as shown below:

<u>Title page,</u>
Items [45] and [*] Notice should read as follows:
-- [45] **Date of Patent: \*Nov. 16, 2004**
  [*] Notice:    Subject to any disclaimer, the term of this patent is extended or adjusted under 35 U.S.C. 154(b) by 0 days.

This Patent is subject to a terminal disclaimer. --

Signed and Sealed this

Seventh Day of June, 2005

JON W. DUDAS
*Director of the United States Patent and Trademark Office*